United States Patent
Patterson et al.

(10) Patent No.: US 9,642,721 B2
(45) Date of Patent: May 9, 2017

(54) IMPLANTS WITH SELF-DEPLOYING ANCHORS

(71) Applicant: Titan Spine, LLC, Mequon, WI (US)

(72) Inventors: Chad J. Patterson, Port Washington, WI (US); Peter F. Ullrich, Jr., Neenah, WI (US)

(73) Assignee: Titan Spine, LLC, Mequon, WI (US)

( * ) Notice: Subject to any disclaimer, the term of this patent is extended or adjusted under 35 U.S.C. 154(b) by 530 days.

(21) Appl. No.: 14/040,899

(22) Filed: Sep. 30, 2013

(65) Prior Publication Data

US 2014/0094921 A1 Apr. 3, 2014

Related U.S. Application Data

(60) Provisional application No. 61/708,681, filed on Oct. 2, 2012.

(51) Int. Cl.
*A61F 2/44* (2006.01)
*A61F 2/30* (2006.01)

(52) U.S. Cl.
CPC ............ *A61F 2/4465* (2013.01); *A61F 2/447* (2013.01); *A61F 2/4455* (2013.01); *A61F 2002/3084* (2013.01); *A61F 2002/30092* (2013.01); *A61F 2002/30093* (2013.01); *A61F 2002/30125* (2013.01); *A61F 2002/30354* (2013.01); *A61F 2002/30383* (2013.01); *A61F 2002/30492* (2013.01); *A61F 2002/30517* (2013.01); *A61F 2002/30579* (2013.01);
(Continued)

(58) Field of Classification Search
CPC ...... A61F 2/4455; A61F 2/446; A61F 2/4465; A61F 2/447

USPC ............................................ 623/17.11–17.16
See application file for complete search history.

(56) References Cited

U.S. PATENT DOCUMENTS

| 4,314,876 A | 2/1982 | Kremer et al. |
| 4,834,757 A | 5/1989 | Brantigan |

(Continued)

FOREIGN PATENT DOCUMENTS

| EP | 0599419 | 6/1994 |
| EP | 0916323 | 5/1999 |

(Continued)

OTHER PUBLICATIONS

Astra Tech Dental, "Nanolevel topographic modifications on the OsseoSpeed surface", http://shop.dentsplyimplants.us, Mar. 8, 2001.

(Continued)

*Primary Examiner* — Mary Hoffman
(74) *Attorney, Agent, or Firm* — Stradley Ronon Stevens & Young, LLP

(57) ABSTRACT

A spinal implant having a top surface, a bottom surface, opposing lateral sides, and opposing anterior and posterior portions. At least one of the top surface and bottom surface has a roughened surface topography, without sharp teeth that risk damage to bone structures, adapted to grip bone through friction generated when the implant is placed between two vertebrae and to inhibit migration of the implant. At least one of the top surface and the bottom surface also includes at least one self-deploying anchor having an expulsion tab and a bone-engaging tip that causes the implant to resist expulsion once the expulsion tab is deployed.

23 Claims, 22 Drawing Sheets

(52) U.S. Cl.
CPC ............... *A61F 2002/30785* (2013.01); *A61F 2002/30828* (2013.01); *A61F 2002/30838* (2013.01); *A61F 2002/30841* (2013.01); *A61F 2002/30906* (2013.01); *A61F 2002/30925* (2013.01); *A61F 2002/448* (2013.01); *A61F 2002/4475* (2013.01); *A61F 2310/00017* (2013.01); *A61F 2310/00023* (2013.01); *A61F 2310/00047* (2013.01); *A61F 2310/00053* (2013.01); *A61F 2310/00131* (2013.01)

(56) References Cited

U.S. PATENT DOCUMENTS

| | | | |
|---|---|---|---|
| 4,904,261 A | 2/1990 | Dove et al. | |
| 5,015,247 A | 5/1991 | Michelson | |
| 5,071,437 A | 12/1991 | Steffee | |
| 5,258,098 A | 11/1993 | Wagner et al. | |
| 5,306,308 A | 4/1994 | Gross et al. | |
| 5,306,309 A | 4/1994 | Wagner et al. | |
| 5,425,772 A | 6/1995 | Brantigan | |
| 5,443,514 A | 8/1995 | Steffee | |
| 5,456,723 A | 10/1995 | Steinemann et al. | |
| 5,507,815 A | 4/1996 | Wagner et al. | |
| 5,571,188 A | 11/1996 | Ellingsen et al. | |
| 5,603,338 A | 2/1997 | Beaty | |
| 5,609,635 A | 3/1997 | Michelson | |
| 5,702,449 A | 12/1997 | McKay | |
| 5,755,798 A | 5/1998 | Papavero et al. | |
| 5,766,252 A | 6/1998 | Henry et al. | |
| 5,776,199 A | 7/1998 | Michelson | |
| 5,849,004 A * | 12/1998 | Bramlet | A61B 17/0401 606/232 |
| 5,860,973 A | 1/1999 | Michelson | |
| 5,863,201 A | 1/1999 | Lazzara et al. | |
| 5,865,845 A | 2/1999 | Thalgott | |
| 5,876,453 A | 3/1999 | Beaty | |
| 5,885,079 A | 3/1999 | Niznick | |
| 5,888,224 A | 3/1999 | Beckers et al. | |
| 5,922,029 A | 7/1999 | Wagner et al. | |
| 5,968,098 A | 10/1999 | Winslow | |
| 5,984,922 A | 11/1999 | McKay | |
| 6,033,582 A | 3/2000 | Lee et al. | |
| 6,039,762 A | 3/2000 | McKay | |
| 6,059,829 A | 5/2000 | Schlapfer et al. | |
| 6,080,158 A | 6/2000 | Lin | |
| 6,086,613 A | 7/2000 | Camino et al. | |
| 6,096,107 A | 8/2000 | Caracostas et al. | |
| 6,123,705 A | 9/2000 | Michelson | |
| 6,143,031 A | 11/2000 | Knothe et al. | |
| 6,143,032 A | 11/2000 | Schafer et al. | |
| 6,176,882 B1 | 1/2001 | Biedermann et al. | |
| 6,179,873 B1 * | 1/2001 | Zientek | A61F 2/4455 623/17.11 |
| 6,183,255 B1 | 2/2001 | Oshida | |
| 6,193,757 B1 | 2/2001 | Foley et al. | |
| 6,193,762 B1 | 2/2001 | Wagner et al. | |
| 6,241,770 B1 | 6/2001 | Michelson | |
| 6,241,771 B1 | 6/2001 | Gresser et al. | |
| 6,245,108 B1 | 6/2001 | Biscup | |
| 6,296,664 B1 | 10/2001 | Middleton | |
| 6,302,914 B1 | 10/2001 | Michelson | |
| 6,342,074 B1 | 1/2002 | Simpson | |
| 6,344,057 B1 | 2/2002 | Rabbe et al. | |
| 6,350,283 B1 | 2/2002 | Michelson | |
| 6,375,681 B1 | 4/2002 | Truscott | |
| 6,387,130 B1 | 5/2002 | Stone et al. | |
| 6,395,031 B1 | 5/2002 | Foley et al. | |
| 6,423,095 B1 | 7/2002 | Van Hoeck et al. | |
| 6,425,920 B1 | 7/2002 | Hamada | |
| 6,432,140 B1 | 8/2002 | Lin | |
| 6,436,102 B1 | 8/2002 | Ralph et al. | |
| 6,447,544 B1 | 9/2002 | Michelson | |
| 6,447,546 B1 * | 9/2002 | Bramlet | A61F 2/446 623/17.11 |
| 6,458,159 B1 | 10/2002 | Thalgott | |
| 6,478,823 B1 | 11/2002 | Michelson | |
| 6,482,233 B1 | 11/2002 | Aebi et al. | |
| 6,485,517 B1 | 11/2002 | Michelson | |
| 6,491,723 B1 | 12/2002 | Beaty | |
| 6,520,993 B2 | 2/2003 | James et al. | |
| 6,558,424 B2 | 5/2003 | Thalgott | |
| 6,569,201 B2 | 5/2003 | Moumene et al. | |
| 6,579,318 B2 | 6/2003 | Varga et al. | |
| 6,592,624 B1 | 7/2003 | Fraser et al. | |
| 6,599,322 B1 | 7/2003 | Amrich et al. | |
| 6,610,089 B1 | 8/2003 | Liu et al. | |
| 6,620,332 B2 | 9/2003 | Amrich | |
| 6,635,086 B2 | 10/2003 | Lin | |
| 6,652,765 B1 | 11/2003 | Beaty | |
| 6,676,703 B2 | 1/2004 | Biscup | |
| 6,702,855 B1 | 3/2004 | Steinemann et al. | |
| 6,719,794 B2 | 4/2004 | Gerber et al. | |
| 6,726,720 B2 | 4/2004 | Ross et al. | |
| 6,730,127 B2 | 5/2004 | Michelson | |
| 6,740,118 B2 | 5/2004 | Eisermann et al. | |
| 6,743,231 B1 | 6/2004 | Gray et al. | |
| 6,758,849 B1 | 7/2004 | Michelson | |
| 6,833,006 B2 | 12/2004 | Foley et al. | |
| 6,890,355 B2 | 5/2005 | Michelson | |
| 6,902,581 B2 | 6/2005 | Walkenhorst et al. | |
| 6,911,249 B2 | 6/2005 | Wagner et al. | |
| 6,923,810 B1 | 8/2005 | Michelson | |
| 6,964,687 B1 | 11/2005 | Bernard et al. | |
| 6,974,480 B2 | 12/2005 | Messerli et al. | |
| 6,981,975 B2 | 1/2006 | Michelson | |
| 7,018,412 B2 | 3/2006 | Ferreira et al. | |
| 7,018,418 B2 | 3/2006 | Amrich et al. | |
| 7,041,137 B2 | 5/2006 | Fulton et al. | |
| 7,044,972 B2 | 5/2006 | Mathys, Jr. et al. | |
| 7,048,870 B1 | 5/2006 | Ellingsen et al. | |
| 7,060,073 B2 | 6/2006 | Frey et al. | |
| 7,066,961 B2 | 6/2006 | Michelson | |
| 7,077,864 B2 | 7/2006 | Byrd, III et al. | |
| 7,087,085 B2 | 8/2006 | Steinemann et al. | |
| 7,112,224 B2 | 9/2006 | Liu et al. | |
| 7,128,760 B2 | 10/2006 | Michelson | |
| 7,137,997 B2 | 11/2006 | Paul | |
| 7,141,068 B2 | 11/2006 | Ross et al. | |
| 7,144,428 B2 | 12/2006 | Anitua | |
| 7,166,129 B2 | 1/2007 | Michelson | |
| 7,169,183 B2 | 1/2007 | Liu et al. | |
| D539,934 S | 4/2007 | Blain | |
| 7,201,775 B2 | 4/2007 | Gorensek et al. | |
| D541,940 S | 5/2007 | Blain | |
| 7,220,280 B2 | 5/2007 | Kast et al. | |
| 7,223,289 B2 * | 5/2007 | Trieu | A61F 2/442 606/151 |
| 7,226,480 B2 | 6/2007 | Thalgott | |
| 7,238,186 B2 | 7/2007 | Zdeblick et al. | |
| 7,238,203 B2 | 7/2007 | Bagga et al. | |
| 7,244,275 B2 | 7/2007 | Michelson | |
| 7,250,060 B2 | 7/2007 | Trieu | |
| 7,255,698 B2 | 8/2007 | Michelson | |
| 7,288,093 B2 | 10/2007 | Michelson | |
| 7,311,734 B2 | 12/2007 | Van Hoeck et al. | |
| D564,095 S | 3/2008 | Blain | |
| 7,347,873 B2 | 3/2008 | Paul et al. | |
| D566,276 S | 4/2008 | Blain | |
| 7,368,065 B2 | 5/2008 | Yang et al. | |
| 7,410,501 B2 | 8/2008 | Michelson | |
| 7,501,073 B2 | 3/2009 | Wen et al. | |
| 7,503,933 B2 | 3/2009 | Michelson | |
| 7,517,363 B2 | 4/2009 | Rogers et al. | |
| D599,019 S | 8/2009 | Pimenta et al. | |
| 7,569,074 B2 | 8/2009 | Eisermann et al. | |
| 7,608,107 B2 | 10/2009 | Michelson | |
| 7,615,078 B2 | 11/2009 | White et al. | |
| 7,655,042 B2 | 2/2010 | Foley et al. | |
| 7,662,186 B2 | 2/2010 | Bagga et al. | |
| 7,662,190 B2 | 2/2010 | Steinemann et al. | |
| 7,744,612 B2 | 6/2010 | Blain | |
| 7,846,183 B2 | 12/2010 | Blain | |
| 7,901,462 B2 | 3/2011 | Yang et al. | |
| 7,998,172 B2 | 8/2011 | Blain | |

(56) References Cited

U.S. PATENT DOCUMENTS

| | | |
|---|---|---|
| 8,062,304 B2 | 11/2011 | Blain et al. |
| 8,100,955 B2 | 1/2012 | Blain et al. |
| 8,114,131 B2 * | 2/2012 | Kohm ............... A61B 17/7065 606/248 |
| 8,142,355 B2 | 3/2012 | Blain et al. |
| 8,172,854 B2 | 5/2012 | Blain et al. |
| 8,262,737 B2 | 9/2012 | Bagga et al. |
| 8,303,660 B1 * | 11/2012 | Abdou ..................... A61F 2/44 623/17.14 |
| 8,523,946 B1 * | 9/2013 | Swann ................... A61F 2/447 623/17.11 |
| 8,657,860 B2 * | 2/2014 | Biedermann ......... A61B 17/68 606/313 |
| 8,894,652 B2 * | 11/2014 | Seifert ............... A61B 17/1617 606/79 |
| 9,044,313 B2 * | 6/2015 | Heaven ................ A61F 2/0805 |
| 9,198,764 B2 * | 12/2015 | Greenberg ............. A61F 2/442 |
| 2001/0014826 A1 | 8/2001 | Biedermann et al. |
| 2001/0016777 A1 | 8/2001 | Biscup |
| 2001/0039454 A1 | 11/2001 | Ricci et al. |
| 2001/0047208 A1 | 11/2001 | Michelson |
| 2002/0049497 A1 | 4/2002 | Mason |
| 2002/0087212 A1 | 7/2002 | James et al. |
| 2002/0099443 A1 | 7/2002 | Messerli et al. |
| 2002/0128713 A1 * | 9/2002 | Ferree ................ A61F 2/30742 623/17.11 |
| 2002/0128716 A1 | 9/2002 | Cohen et al. |
| 2002/0138142 A1 | 9/2002 | Castro et al. |
| 2002/0156529 A1 | 10/2002 | Li et al. |
| 2002/0161443 A1 | 10/2002 | Michelson |
| 2002/0173854 A1 | 11/2002 | Amrich |
| 2002/0188294 A1 | 12/2002 | Couture et al. |
| 2003/0014116 A1 | 1/2003 | Ralph et al. |
| 2003/0083668 A1 | 5/2003 | Rogers et al. |
| 2003/0105527 A1 | 6/2003 | Bresina |
| 2003/0109928 A1 | 6/2003 | Pasquet et al. |
| 2003/0153975 A1 | 8/2003 | Byrd, III et al. |
| 2003/0176925 A1 | 9/2003 | Paponneau |
| 2003/0181980 A1 | 9/2003 | Berry et al. |
| 2003/0181981 A1 | 9/2003 | Lemaire |
| 2003/0187436 A1 * | 10/2003 | Bolger ............... A61B 17/0206 623/17.11 |
| 2003/0187506 A1 | 10/2003 | Ross et al. |
| 2003/0191531 A1 | 10/2003 | Berry et al. |
| 2004/0010312 A1 * | 1/2004 | Enayati ................. A61F 2/446 623/17.11 |
| 2004/0073314 A1 | 4/2004 | White et al. |
| 2004/0117019 A1 | 6/2004 | Trieu et al. |
| 2004/0117020 A1 | 6/2004 | Frey et al. |
| 2004/0122518 A1 | 6/2004 | Rhoda |
| 2004/0127993 A1 | 7/2004 | Kast et al. |
| 2004/0134886 A1 | 7/2004 | Wagner et al. |
| 2004/0153154 A1 | 8/2004 | Dinkelacker |
| 2004/0153160 A1 | 8/2004 | Carrasco |
| 2004/0162616 A1 | 8/2004 | Simonton et al. |
| 2004/0167632 A1 | 8/2004 | Wen et al. |
| 2004/0210309 A1 | 10/2004 | Denzer et al. |
| 2004/0230306 A1 | 11/2004 | Hoeck et al. |
| 2004/0265780 A1 | 12/2004 | Robb et al. |
| 2004/0267367 A1 | 12/2004 | O'Neil |
| 2005/0021150 A1 | 1/2005 | Michelson |
| 2005/0027360 A1 | 2/2005 | Webb et al. |
| 2005/0038512 A1 | 2/2005 | Michelson |
| 2005/0049590 A1 * | 3/2005 | Alleyne ................. A61F 2/442 623/17.11 |
| 2005/0060034 A1 | 3/2005 | Berry et al. |
| 2005/0075734 A1 | 4/2005 | Fulton et al. |
| 2005/0085913 A1 | 4/2005 | Fraser et al. |
| 2005/0119758 A1 | 6/2005 | Alexander et al. |
| 2005/0131416 A1 | 6/2005 | Jansen et al. |
| 2005/0147942 A1 | 7/2005 | Hall |
| 2005/0159814 A1 | 7/2005 | Karahalios |
| 2005/0161120 A1 | 7/2005 | Inagaki et al. |
| 2005/0165483 A1 | 7/2005 | Ray et al. |
| 2005/0203630 A1 | 9/2005 | Pope et al. |
| 2005/0222681 A1 | 10/2005 | Richley et al. |
| 2005/0251257 A1 | 11/2005 | Mitchell et al. |
| 2006/0004453 A1 * | 1/2006 | Bartish, Jr. ........... A61F 2/4425 623/17.15 |
| 2006/0041313 A1 | 2/2006 | Allard et al. |
| 2006/0093646 A1 | 5/2006 | Cima et al. |
| 2006/0095136 A1 * | 5/2006 | McLuen ............... A61F 2/4455 623/23.47 |
| 2006/0100705 A1 | 5/2006 | Puno et al. |
| 2006/0149372 A1 | 7/2006 | Paxson et al. |
| 2006/0149376 A1 | 7/2006 | Shimp et al. |
| 2006/0167549 A1 | 7/2006 | Mathys, Jr. et al. |
| 2006/0190079 A1 | 8/2006 | Istephanous et al. |
| 2006/0219661 A1 | 10/2006 | Towse et al. |
| 2006/0235534 A1 | 10/2006 | Gertzman et al. |
| 2006/0265065 A1 | 11/2006 | Bagga et al. |
| 2006/0293748 A1 | 12/2006 | Alexander et al. |
| 2007/0010885 A1 | 1/2007 | Liu et al. |
| 2007/0032790 A1 * | 2/2007 | Aschmann ......... A61B 17/7065 606/249 |
| 2007/0093898 A1 | 4/2007 | Schwab et al. |
| 2007/0118220 A1 | 5/2007 | Liu et al. |
| 2007/0118223 A1 | 5/2007 | Allard et al. |
| 2007/0191958 A1 | 8/2007 | Abdou |
| 2007/0233247 A1 | 10/2007 | Schwab |
| 2007/0233248 A1 | 10/2007 | Schwab et al. |
| 2007/0260320 A1 | 11/2007 | Peterman et al. |
| 2007/0269475 A1 | 11/2007 | Gil et al. |
| 2007/0270951 A1 | 11/2007 | Davis et al. |
| 2007/0270956 A1 | 11/2007 | Heinz |
| 2007/0270960 A1 * | 11/2007 | Bonin, Jr. .............. A61F 2/442 623/17.11 |
| 2007/0270961 A1 * | 11/2007 | Ferguson ................ A61F 2/44 623/17.11 |
| 2007/0282441 A1 | 12/2007 | Stream et al. |
| 2007/0288028 A1 | 12/2007 | Gorensek et al. |
| 2007/0293949 A1 | 12/2007 | Salerni et al. |
| 2008/0014243 A1 | 1/2008 | Ellingsen et al. |
| 2008/0071380 A1 | 3/2008 | Sweeney |
| 2008/0077171 A1 | 3/2008 | Blain et al. |
| 2008/0097610 A1 | 4/2008 | Guyer et al. |
| 2008/0154378 A1 | 6/2008 | Pelo |
| 2008/0177306 A1 * | 7/2008 | Lamborne ........... A61B 17/7062 606/246 |
| 2008/0195209 A1 | 8/2008 | Garcia et al. |
| 2008/0221689 A1 | 9/2008 | Chaput et al. |
| 2008/0249622 A1 | 10/2008 | Gray |
| 2008/0269764 A1 | 10/2008 | Blain et al. |
| 2008/0269806 A1 | 10/2008 | Zhang et al. |
| 2008/0288076 A1 | 11/2008 | Soo et al. |
| 2009/0005784 A1 | 1/2009 | Blain et al. |
| 2009/0005871 A1 | 1/2009 | White et al. |
| 2009/0014243 A1 | 1/2009 | Whigham |
| 2009/0024132 A1 | 1/2009 | Blain et al. |
| 2009/0054988 A1 * | 2/2009 | Hess .................... A61B 17/025 623/17.16 |
| 2009/0082819 A1 | 3/2009 | Blain et al. |
| 2009/0088800 A1 | 4/2009 | Blain et al. |
| 2009/0088853 A1 | 4/2009 | Ogilvie et al. |
| 2009/0132048 A1 | 5/2009 | Denzer |
| 2009/0164020 A1 * | 6/2009 | Janowski ............... A61F 2/4465 623/17.16 |
| 2009/0182432 A1 | 7/2009 | Zdeblick et al. |
| 2009/0187247 A1 | 7/2009 | Metcalf, Jr. et al. |
| 2009/0204152 A1 | 8/2009 | Blain |
| 2009/0234362 A1 | 9/2009 | Blain et al. |
| 2009/0264928 A1 | 10/2009 | Blain |
| 2009/0265007 A1 * | 10/2009 | Colleran ............... A61F 2/4465 623/17.16 |
| 2009/0276049 A1 | 11/2009 | Weiland |
| 2009/0312837 A1 | 12/2009 | Eisermann et al. |
| 2010/0036496 A1 * | 2/2010 | Yu ...................... A61F 2/4425 623/17.14 |
| 2010/0076559 A1 | 3/2010 | Bagga et al. |
| 2010/0094426 A1 | 4/2010 | Grohowski, Jr. et al. |
| 2010/0121385 A1 | 5/2010 | Blain et al. |

(56) References Cited

U.S. PATENT DOCUMENTS

| | | | |
|---|---|---|---|
| 2010/0137989 A1* | 6/2010 | Armstrong | A61F 2/4465 623/17.16 |
| 2010/0161062 A1 | 6/2010 | Foley et al. | |
| 2010/0173264 A1 | 7/2010 | Fredriksson et al. | |
| 2010/0174382 A1* | 7/2010 | Gretzer | A61L 27/306 623/23.53 |
| 2010/0204798 A1 | 8/2010 | Gerbec et al. | |
| 2010/0218854 A1 | 9/2010 | Garcia Saban et al. | |
| 2010/0228288 A1 | 9/2010 | Blain | |
| 2010/0249937 A1 | 9/2010 | Blain et al. | |
| 2010/0274286 A1 | 10/2010 | Blain et al. | |
| 2010/0274358 A1 | 10/2010 | Mueller et al. | |
| 2010/0303722 A1 | 12/2010 | Jin et al. | |
| 2011/0009965 A1 | 1/2011 | Ankem | |
| 2011/0035007 A1* | 2/2011 | Patel | A61F 2/4465 623/17.11 |
| 2011/0040301 A1 | 2/2011 | Blain et al. | |
| 2011/0082503 A1 | 4/2011 | Blain | |
| 2011/0190902 A1 | 8/2011 | Tong et al. | |
| 2011/0224796 A1 | 9/2011 | Weiland et al. | |
| 2011/0230970 A1 | 9/2011 | Lynn et al. | |
| 2011/0230971 A1* | 9/2011 | Donner | A61B 17/70 623/17.16 |
| 2011/0233169 A1 | 9/2011 | Mayfield et al. | |
| 2011/0282454 A1 | 11/2011 | Ullrich, Jr. et al. | |
| 2012/0009341 A1 | 1/2012 | Noh et al. | |
| 2012/0046695 A9 | 2/2012 | Blain | |
| 2012/0078371 A1* | 3/2012 | Gamache | A61F 2/4465 623/17.16 |
| 2012/0095561 A1 | 4/2012 | Voisard et al. | |
| 2012/0123424 A1 | 5/2012 | Blain et al. | |
| 2012/0123548 A1 | 5/2012 | Lynn et al. | |
| 2012/0136443 A1 | 5/2012 | Wenzel | |
| 2012/0149991 A1 | 6/2012 | Blain et al. | |
| 2012/0158056 A1 | 6/2012 | Blain | |
| 2012/0158144 A1 | 6/2012 | Ullrich, Jr. et al. | |
| 2012/0172991 A1 | 7/2012 | Bertele et al. | |
| 2012/0197404 A1 | 8/2012 | Brun et al. | |
| 2012/0232664 A1 | 9/2012 | Ulrich, Jr. et al. | |
| 2012/0239150 A1 | 9/2012 | Ullrich, Jr. et al. | |
| 2012/0239151 A1 | 9/2012 | Ulrich, Jr. et al. | |
| 2012/0239152 A1 | 9/2012 | Ullrich, Jr. et al. | |
| 2012/0239153 A1 | 9/2012 | Ullrich, Jr. et al. | |
| 2012/0239154 A1 | 9/2012 | Ullrich, Jr. et al. | |
| 2012/0245694 A1 | 9/2012 | Ullrich, Jr. et al. | |
| 2012/0277876 A1 | 11/2012 | Ullrich, Jr. et al. | |
| 2012/0303127 A1 | 11/2012 | Ullrich, Jr. et al. | |
| 2012/0303128 A1 | 11/2012 | Ullrich, Jr. et al. | |
| 2012/0303129 A1 | 11/2012 | Bagga et al. | |
| 2012/0310354 A1 | 12/2012 | Ullrich, Jr. et al. | |
| 2012/0312778 A1 | 12/2012 | Ullrich, Jr. et al. | |
| 2012/0312779 A1 | 12/2012 | Patterson et al. | |
| 2012/0316650 A1 | 12/2012 | Ullrich, Jr. et al. | |
| 2012/0316651 A1 | 12/2012 | Ullrich, Jr. et al. | |
| 2012/0316653 A1 | 12/2012 | Ullrich, Jr. et al. | |
| 2013/0006363 A1 | 1/2013 | Ullrich, Jr. et al. | |
| 2013/0150968 A1* | 6/2013 | Dinville | A61F 2/447 623/17.16 |
| 2013/0226300 A1* | 8/2013 | Chataigner | A61F 2/442 623/17.16 |
| 2013/0245767 A1* | 9/2013 | Lee | A61F 2/447 623/17.16 |
| 2014/0180417 A1* | 6/2014 | Bergey | A61F 2/4455 623/17.16 |
| 2014/0379085 A1* | 12/2014 | Duffield | A61F 2/4455 623/17.16 |

FOREIGN PATENT DOCUMENTS

| | | |
|---|---|---|
| EP | 1449544 | 8/2004 |
| EP | 2386274 | 11/2011 |
| JP | 08010276 | 1/1996 |
| JP | 19968010276 | 1/1996 |
| JP | 2001170092 | 6/2001 |
| WO | 9706753 | 2/1997 |
| WO | 98/01091 | 1/1998 |
| WO | 0128469 | 4/2001 |
| WO | 0170144 | 9/2001 |
| WO | 0195838 | 12/2001 |
| WO | 2004008983 | 1/2004 |
| WO | 2004041131 | 5/2004 |
| WO | 2006081843 | 8/2006 |
| WO | 2006116306 | 11/2006 |
| WO | 2006119088 | 11/2006 |
| WO | 2006121795 | 11/2006 |
| WO | 2007089905 | 8/2007 |
| WO | 2008103843 | 8/2008 |
| WO | 2009006225 | 1/2009 |
| WO | 2009029458 | 3/2009 |
| WO | 2009129262 | 10/2009 |
| WO | 2009140544 | 11/2009 |
| WO | 2011094748 | 8/2011 |

OTHER PUBLICATIONS

Astra Tech Dental, "OsseoSpeed—more bone more rapidly", http://shop.dentsplyimplants.us, May 2011.

Guo, et al., "The effect of hydrofluoric acid treatment of TiO2 grit blasted titanium implants on adherent osteoblast gene expression in vitro and in vivo", Biomaterials 28 (Sep. 14, 2007) 5418-5425.

He, et al., "Mechanical and Histomorphometric Evaluations of Rough Titanium Implants Treated with Hydrofluoric Acid/Nitric Acid Solution in Rabbit Tibia", Int. J. Oral Maxillofac. Implants, Nov. 1, 2011; 26:115-122.

Isa, et al., "Effects of Fluoride-Modified Titanium Surfaces on Osteoblast Proliferation and Gene Expression", Int. J. Oral Maxillofac. Implants 2006; 21:203-211.

Lamolle, et al., "The effect of hydrofluoric acid treatment of titanium surface on nanostructural and chemical changes and the growith of MC3T3-E1 cells", Biomaterials 30 (Nov. 20, 2008) 736-742.

Meirelles, et al., "The Effect of Chemical and Nanotopographical Modifications on the Early Stages of Osseointegration", Int. J. Oral Maxillofac. Implants 2008; 23:641-647.

Pending U.S. Appl. No. 13/286,813 of Chad J. Patterson, et al. filed Nov. 1, 2011.

Pending U.S. Appl. No. 13/713,417 of Chad J. Patterson, et al. filed Dec. 13, 2012.

Pending U.S. Appl. No. 13/784,144 of Peter F. Ullrich, Jr., et al. filed Mar. 4, 2013.

Pending U.S. Appl. No. 13/826,304 of Peter F. Ullrich, Jr., et al. filed Mar. 14, 2013.

Supplementary Partial European Search Report issued Aug. 19, 2011, for EP 06 75 9086.

Supplementary Partial European Search Report issued Sep. 27, 2011, for EP 06 75 9086.

Variola, et al., "Nanoscale surface modifications of medically relevant metals: state-of-the art and prespectives", Nanoscale, 2011, 3, 335-353.

Wennerberg, A., et al., "Effects of titanium surface topography on bone integration: a systematic review", Clin. Oral Impl. Res., 20 (Suppl. 4), 2009, pp. 172-184.

Wennerberg, et al., "Spontaneously formed nanostructures on titanium surfaces", Clin. Oral Impl. Res., 2012, 1-7.

* cited by examiner

IMPLANTS WITH SELF-DEPLOYING ANCHORS

CROSS REFERENCE TO RELATED APPLICATION

This application is a non-provisional application of U.S. provisional application No. 61/708,681 filed Oct. 2, 2012, the contents of which are incorporated by reference into this document in its entirety for all purposes.

TECHNICAL FIELD

The present invention relates generally to interbody spinal implants and, more particularly, to spinal implants having one or more self-deploying anchors.

BACKGROUND OF THE INVENTION

In the simplest terms, the spine is a column made of vertebrae and discs. The vertebrae provide the support and structure of the spine while the spinal discs, located between the vertebrae, act as cushions or "shock absorbers." These discs also contribute to the flexibility and motion of the spinal column. Over time, the discs may become diseased or infected, may develop deformities such as tears or cracks, or may simply lose structural integrity (e.g., the discs may bulge or flatten). Impaired discs can affect the anatomical functions of the vertebrae, due to the resultant lack of proper biomechanical support, and are often associated with chronic back pain.

Several surgical techniques have been developed to address spinal defects, such as disc degeneration and deformity. Spinal fusion has become a recognized surgical procedure for mitigating back pain by restoring biomechanical and anatomical integrity to the spine. Spinal fusion techniques involve the removal, or partial removal, of at least one intervertebral disc and preparation of the disc space for receiving an implant by shaping the exposed vertebral endplates. An implant is then inserted between the opposing endplates.

Spinal fusion procedures can be achieved using a posterior or an anterior approach, for example. Anterior interbody fusion procedures generally have the advantages of reduced operative times and reduced blood loss. Further, anterior procedures do not interfere with the posterior anatomic structure of the lumbar spine. Anterior procedures also minimize scarring within the spinal canal while still achieving improved fusion rates, which is advantageous from a structural and biomechanical perspective. These generally preferred anterior procedures are particularly advantageous in providing improved access to the disc space, and thus correspondingly better endplate preparation.

There are a number of problems, however, with traditional spinal implants including, but not limited to, improper seating of the implant, implant subsidence (defined as sinking or settling) into the softer cancellous bone of the vertebral body, poor biomechanical integrity of the endplates, damaging critical bone structures during or after implantation, and the like. In summary, at least ten separate challenges can be identified as inherent in traditional anterior spinal fusion devices. Such challenges include: (1) end-plate preparation; (2) implant difficulty; (3) materials of construction; (4) implant expulsion; (5) implant subsidence; (6) insufficient room for bone graft; (7) stress shielding; (8) lack of implant incorporation with vertebral bone; (9) limitations on radiographic visualization; and (10) cost of manufacture and inventory.

SUMMARY OF THE INVENTION

The present invention provides for interbody spinal implants having one or more self-deploying anchors on a top integration surface, a bottom integration surface, or both surfaces. The implants may be inserted with the anchor(s) in a retracted position (e.g., substantially coplanar or below the top or bottom surface of the implant) without damaging critical bone structures during or after implantation. After implantation (e.g., once the implant reaches body temperature), the one or more self-deploying anchors may expand to a deployed position (e.g., extending above or beyond the top or bottom surface of the implant). The self-deploying anchors may allow for smaller (e.g., up to 30-40% smaller than traditional implants) and more easily implanted implant bodies. In addition, the location and orientation of the anchors may be selected to help the implant resist expulsion (e.g., due to biological loading from the posterior to the anterior of the interdisk space).

Various implant body shapes are provided to allow for implantation through various access paths to the spine through a patient's body. Certain embodiments of the present invention may be especially suited for placement between adjacent human vertebral bodies. The implants of the present invention may be used in procedures such as Anterior Lumbar Interbody Fusion (ALIF), Posterior Lumbar Interbody Fusion (PLIF), Transforaminal Lumbar Interbody Fusion (TLIF), and cervical fusion.

In one embodiment, the present invention provides a spinal implant having a top surface, a bottom surface, opposing lateral sides, and opposing anterior and posterior portions where at least one of the top surface and bottom surface has a roughened surface topography, without sharp teeth that risk damage to bone structures, adapted to grip bone through friction generated when the implant is placed between two vertebrae and to inhibit migration of the implant, and at least one of the top surface and the bottom surface includes at least one self-deploying anchor having an expulsion tab and a bone-engaging tip that causes the implant to resist expulsion once the expulsion tab is deployed.

The top surface, the bottom surface, or both surfaces of the implant include at least one self-deploying anchor. The self-deploying anchor may be formed from a temperature-sensitive metal alloy, for example, where the anchor is deployed when the implant is raised to or above the transformation temperature of the temperature-sensitive metal alloy (e.g., at or slightly below body temperature). In addition or in the alternative, the anchor may be formed from a shape memory material. For example, the anchor may be formed from nickel-containing alloys (e.g., nickel-titanium alloys, such as nitinol), titanium-containing alloys (e.g., titanium-palladium alloys), copper-containing alloys (e.g., copper-aluminum-nickel or copper-zinc alloys), iron-containing alloys (e.g., iron-platinum alloys), and the like.

The self-deploying anchor may include an expulsion tab having an integration surface and an interior surface opposite the integration surface. The anchor may further include a bone-engaging tip and a connecting end opposite the bone-engaging tip. The integration surface of the expulsion tab may be substantially coplanar with or below the top surface, bottom surface, or both surfaces of the implant when in a retracted condition. After implantation (e.g., once the implant reaches body temperature), the self-deploying anchor(s) may expand to a deployed position where the expulsion tab and bone-engaging tip extend outward and beyond the top surface, bottom surface, or both surfaces of the implant.

The self-deploying anchor may contain a locking mechanism. In particular, the anchor may include a locking bar to lock the anchor in the deployed position. The locking bar may include a locking tip and a connecting end opposite the locking tip. A connecting piece having a first and second end may connect the expulsion tab and the locking bar. For example, the connecting end of the expulsion tab may be coupled to the first end of the connecting piece by a first arcuate member forming a connection bore and the connecting end of the locking bar may be coupled to the second end of the connecting piece by a second arcuate member. The pieces may be directly or indirectly coupled together to form the anchor portion. The interior surface of the expulsion tab may include a protrusion which engages the locking tip of the locking bar and prevents a deployed anchor from returning to a retracted position. In the alternative, the interior surface of the expulsion tab may include a ratchet system having a plurality of protrusions each separated by a recess where the locking tip enters a recess and the protrusion stops the anchor from returning to a retracted state once deployed.

The anchor(s) may be affixed to the implant body using any suitable attachment mechanisms. For example, the anchor(s) may be affixed to the implant with a pin, bolt, shaft, or the like, which extends through the connection bore (and, for example, into the lateral sides of the implant). The anchor may optionally include a second pin, bolt, shaft, or the like, which extends through an opening formed by the second arcuate member.

The top and bottom surfaces of the implant may include any suitable number and placement of anchors in order to minimize or resist expulsion. For example, one, two, three, or more anchors may be positioned on each of the top and bottom surfaces. In one embodiment, the implant includes at least three self-deploying anchors, and the bone-engaging tips of each of the anchors are oriented substantially toward the anterior portion of the implant and may be located, for example, proximate the anterior portion of the implant. In another embodiment, the implant includes at least two self-deploying anchors and the bone-engaging tips are oriented in opposite directions (e.g., positioned substantially centrally on the top surface, the bottom surface, or both surfaces of the implant). As one example, the bone-engaging tip of the first self-deploying anchor may be oriented substantially toward the anterior portion of the implant and the bone-engaging tip of the second self-deploying anchor may be oriented substantially toward the posterior portion of the implant.

The top surface, bottom surface, or both surfaces of the implant, which may be defined as integration surfaces, as well as the top surface or integration surface of the one or more anchors may have a roughened surface topography. The integration surface of the self-deploying anchor may have a roughened surface topography that is the same as or different from the integration surfaces of the implant. The integration surface(s) may have fusion and biologically active surface geometry, for example, in regular repeating patterns. The integration surface(s) may include macro features, micro features, and nano features. For example, the features may include a repeating pattern of smooth shapes oriented in opposition to the biologic forces on the implant and to the insertion direction.

The roughened surface topography may be fabricated, for example, using macro processing, micro processing, and nano processing techniques. The macro, micro, and nano process may include mechanical or chemical removal of at least a portion of the surface. For example, the macro features may be formed by heavy mechanical or chemical bulk removal, the micro features may be formed by mechanical or chemical removal, and the nano features may be formed by mild chemical etching, laser or other directed energy material removal, abrasion, blasting, or tumbling.

For example, the macro features may have a mean spacing between about 400-2,000 microns, a maximum peak-to-valley height between about 40-500 microns, and an average amplitude between about 20-200 microns; the micro features may have a mean spacing between about 20-400 microns, a maximum peak-to-valley height between about 2-40 microns, and an average amplitude between about 1-20 microns; and the nano features may have a mean spacing between about 0.5-20 microns, a maximum peak-to-valley height between about 0.2-2 microns, and an average amplitude between about 0.01-1 microns.

The implant may be fabricated from any suitable material. For example, the implant may be comprised of a metal, such as titanium. In the case of a composite implant (e.g., a body with one or more integration plates), the implant body may be fabricated from a non-metallic material, non-limiting examples of which include polyetherether-ketone, hedrocel, ultra-high molecular weight polyethylene, and combinations thereof. The implant body may be fabricated from both a metal and a non-metallic material to form a composite implant. For example, a composite implant may be formed with integration plates made of titanium combined with a polymeric body.

The implant may comprise a solid body or may comprise a substantially hollow center and a vertical aperture. For example, the vertical aperture may (a) extend from the top surface to the bottom surface, (b) have a size and shape predetermined to maximize the surface area of the top surface and the bottom surface available proximate the anterior and posterior portions while maximizing both radiographic visualization and access to the substantially hollow center, and (c) define a transverse rim.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

Figure 1A:
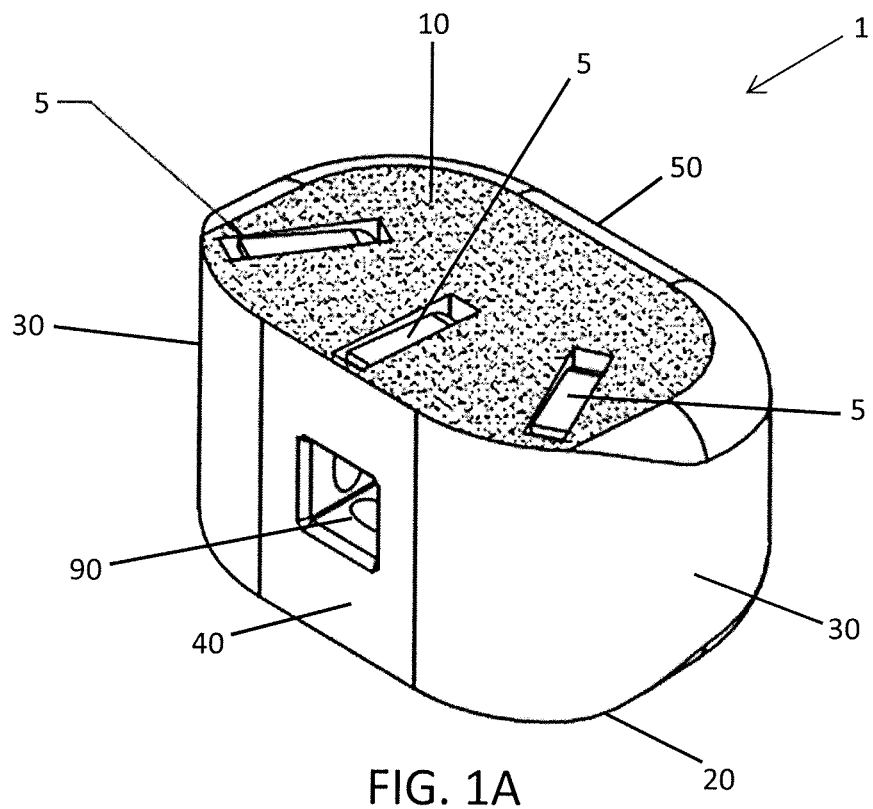
FIG. 1A shows a perspective view of an embodiment of the interbody spinal implant having three self-deploying anchors in a retracted condition.

The present invention provides for spinal implants having at least one self-deploying anchor on the top surface, the bottom surface, or both surfaces of the implant. The implant has contained within the body of the implant tabs or anchoring tips that expand after they are placed within the interdisk area of the spine. The self-deploying anchors are designed to open, extend, or deploy, for example, once the anchor material reaches near or about body temperature. Each anchor may include an expulsion tab and a bone-engaging tip that causes the implant to resist expulsion once the expulsion tab is deployed. A locking mechanism may also be provided to hold the bone-engaging tip in position and prevent the anchor from collapsing or returning to the retracted position.

Anchor(s)

The spinal implants include at least one self-deploying anchor. As used in this document, "self-deploying anchor" includes an anchor or a portion of an anchor that deploys, expands, or extends once a certain condition is met (e.g., temperature sensitive or shape memory). The anchor does not require any type of physical or manual manipulation in order to be deployed. In other words, the anchor deploys by itself when the necessary condition is met. The anchor may be in a "retracted" condition, state, or position meaning that the anchor is housed substantially or completely within the body of the implant. In other words, the anchor or a portion of the anchor is not extending beyond any surface of the implant. The anchor may be in a "deployed" condition, state, or position meaning that the anchor or a portion of the anchor extends outside or opens beyond the periphery of the body of the implant. In other words, the anchor or a portion of the anchor is extending beyond at least one surface of the implant.

The self-deploying anchor may be formed from a temperature-sensitive material (e.g., a thermal shape memory material) or a mechanical shape memory material, for example. As will be recognized by one of ordinary skill in the art, temperature-sensitive materials and shape memory materials are capable of remembering a previously memorized shape or position. In the case of a temperature-sensitive material, the anchor remains in a retracted state until the anchor is raised to or above a given temperature, for example, the transformation temperature of a temperature-sensitive metal alloy. The transformation temperature is a temperature at which a change in phase occurs. For example, the temperature-sensitive material can transition between martensite and austenite phases. Thus, the temperature-sensitive material may be deformed (e.g., placed in a retracted position of the anchor) in the martensite phase where it will remain deformed until heated to the austenite phase where it will return to its pre-deformed shape (e.g., move to a deployed position of the anchor). In other words, once the anchor is raised to or above the transformation temperature, the anchor is deployed and returns to its memorized shape. The transformation temperature may be any temperature above room temperature (above about 20-25° C. (68-77° F.)) up to and including about body temperature (37.0° C.±about 0.5° C. (98.6° F.±about 0.9° F.)), for example. The exact transformation temperature depends on the material selected (e.g., the nickel/titanium ratio of the alloy). Preferably, the transformation temperature ranges from about 25° C. to about 37° C., and preferably about 30° C. to about 37° C. The shape memory materials behave in a similar manner, but the condition that causes change may be revealing or exposing the portion of the anchor to be deployed. For example, the anchor may be held in the retracted position (e.g., by a sleeve) and the anchor is deployed when the sleeve is removed and the implant is implanted.

The anchor or any portion of the anchor (e.g., the expulsion tab) may be formed from any suitable temperature-sensitive or shape memory material. For example, the anchor may be formed from nickel-containing alloys (e.g., nickel-titanium alloys, such as nitinol), titanium-containing alloys (e.g., titanium-palladium alloys), copper-containing alloys (e.g., copper-aluminum-nickel or copper-zinc alloys), iron-containing alloys (e.g., iron-platinum alloys), and the like. In an exemplary embodiment, the expulsion tab or the entire anchor is formed from a nickel-titanium alloy, such as nitinol.

Figure 1B:
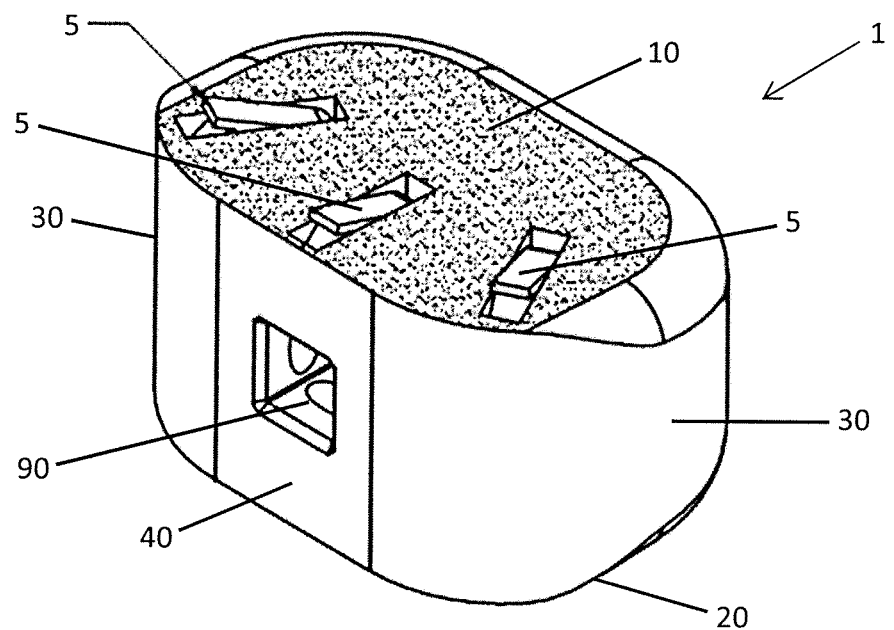
FIG. 1B shows a perspective view of the embodiment depicted in FIG. 1A with the three self-deploying anchors in a deployed condition.
Figure 2A:
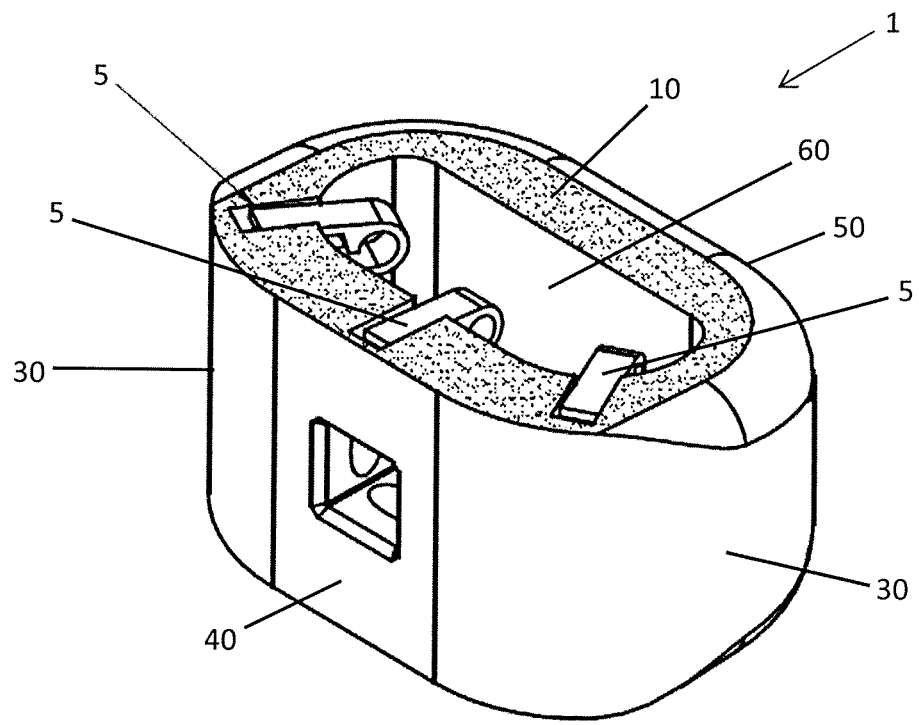
FIG. 2A shows a perspective view of an embodiment of the interbody spinal implant with a substantially hollow center and a single vertical aperture and having three self-deploying anchors in a retracted condition.
Figure 2B:
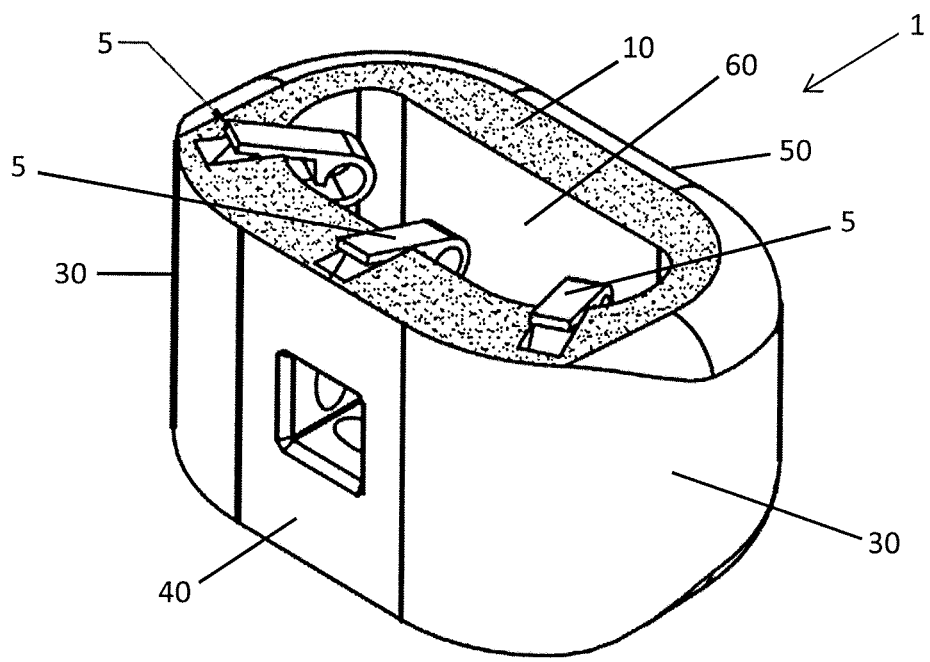
FIG. 2B shows a perspective view of the embodiment depicted in FIG. 2A with the three self-deploying anchors in a deployed condition.
Figure 9A:
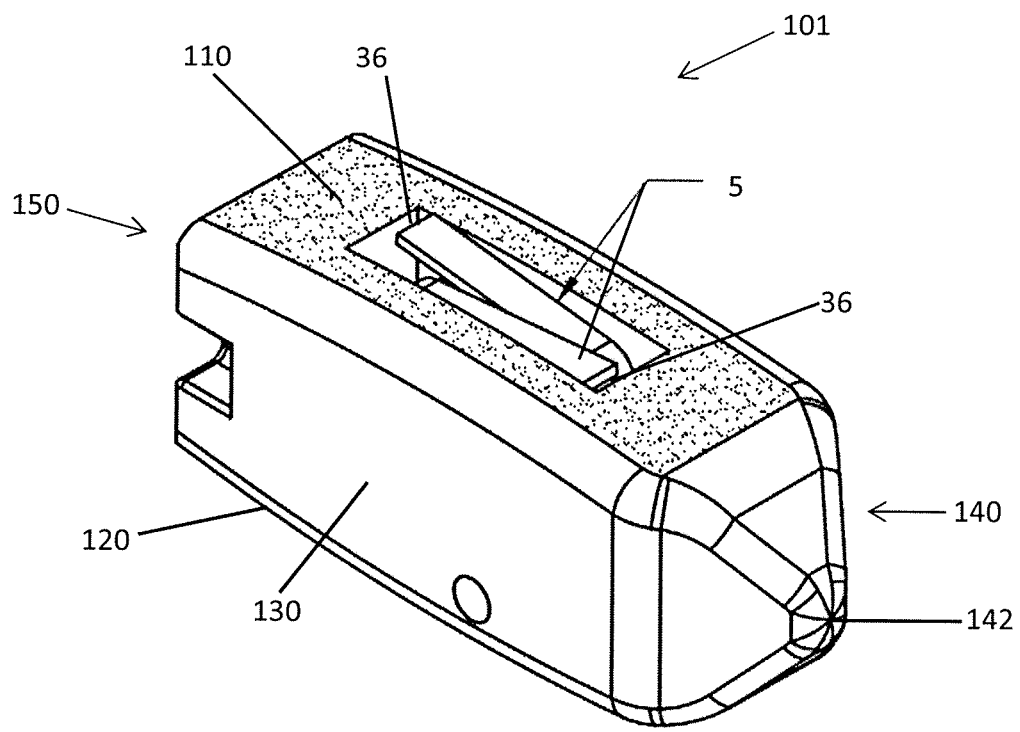
FIG. 9A shows a perspective view of an embodiment of the interbody spinal implant having two self-deploying anchors positioned in opposite directions in a retracted condition.
Figure 9B:
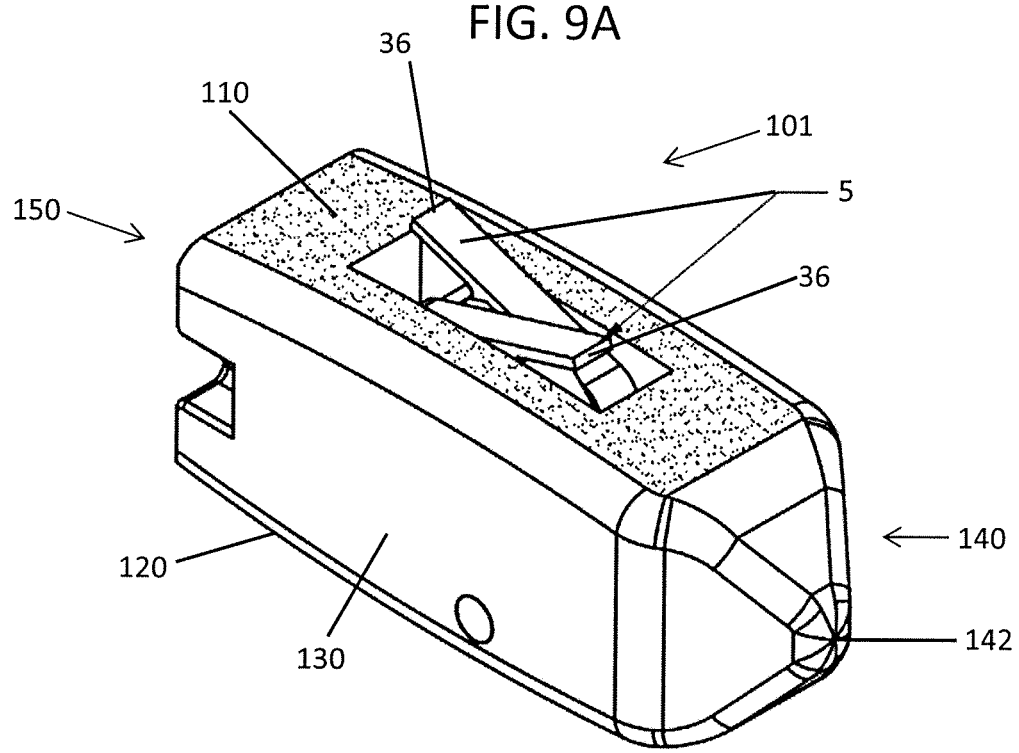
FIG. 9B shows a perspective view of the embodiment depicted in FIG. 9A with the self-deploying anchors in a deployed condition.
Figure 13A:
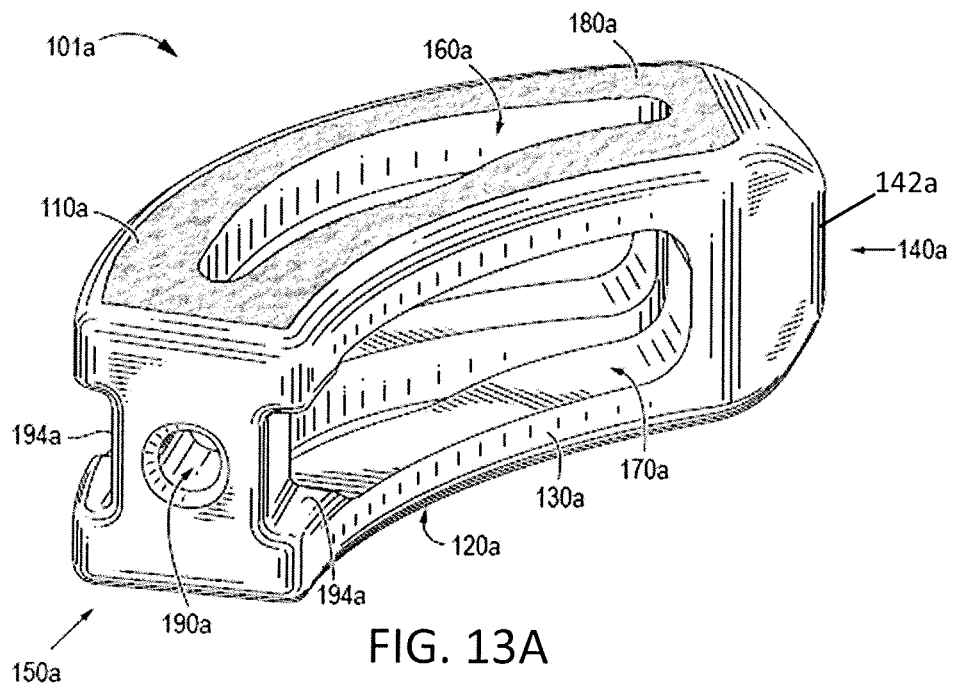
FIG. 13A shows a perspective view from the front of an embodiment of the interbody spinal implant according to the present invention.
Figure 13B:
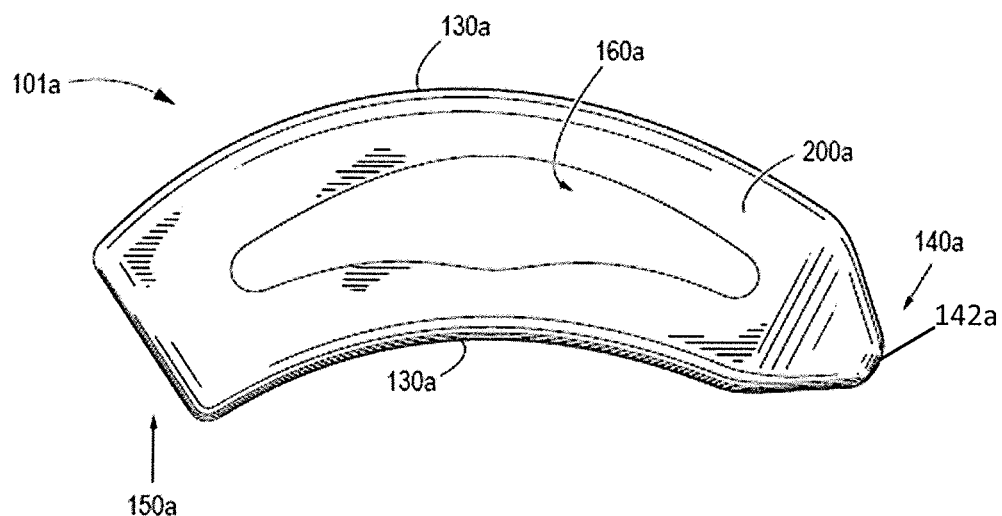
FIG. 13B is a top view of the interbody spinal implant illustrated in FIG. 13A.
Figure 17:
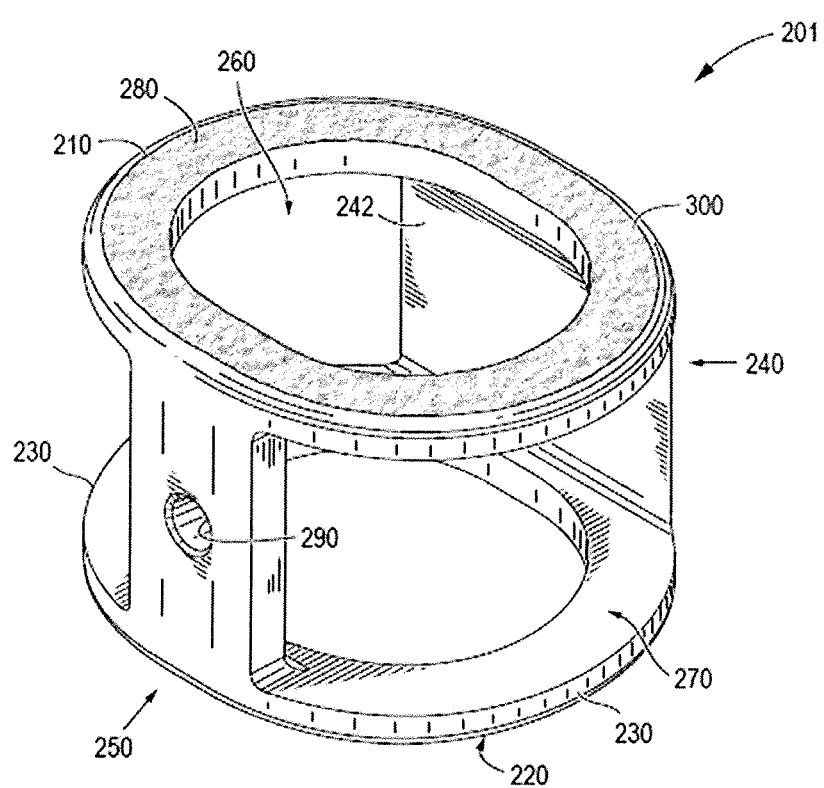
FIG. 17 shows a perspective view of an embodiment of the interbody spinal implant having a generally oval shape and being especially well adapted for use in a cervical spine surgical procedure.
Figure 19:
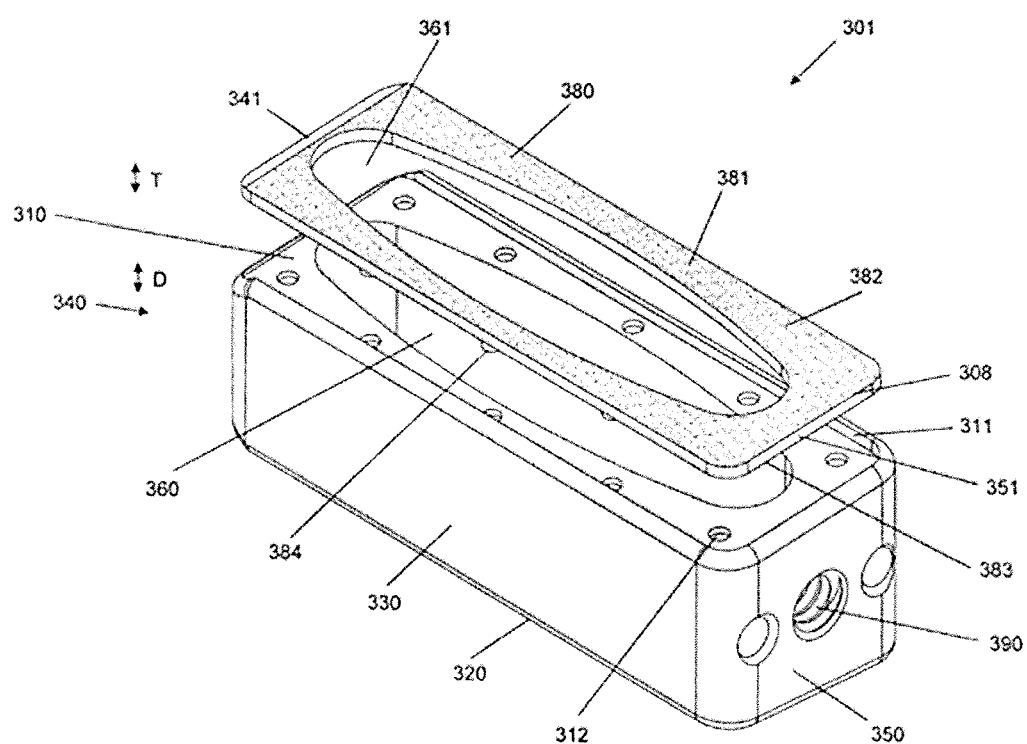
FIG. 19 shows an exploded view of a lateral lumbar implant with an integration plate.

Referring now to the drawing, in which like reference numbers refer to like elements throughout the various figures that comprise the drawing, the interbody spinal implant 1, 101, 101a, 201, and 301 includes a top surface 10, 110, 110a, 210, and 310, a bottom surface 20, 120, 120a, 220, and 320, opposing lateral sides 30, 130, 130a, 230, and 330, and opposing anterior 40, 140, 140a, 240, and 340 and posterior 50, 150, 150a, 250, and 350 portions. The top surface includes three self-deploying anchors 5 in a retracted condition (FIG. 1A) and a deployed condition (FIG. 1B). FIGS. 1A and 1B show perspective views of one embodiment of the interbody spinal implant 1 especially well adapted for use in an Anterior Lumbar Interbody Fusion (ALIF) procedure. FIGS. 9A and 9B show perspective views of one embodiment of the interbody spinal implant 101 especially well adapted for use in Posterior Lumbar Interbody Fusion (PLIF). FIGS. 13A and 13B show perspective views of one embodiment of the interbody spinal implant 101a especially well adapted for use in Transforaminal Lumbar Interbody Fusion (TLIF). FIG. 17 shows a perspective view of one embodiment of the interbody spinal implant 201 especially well adapted for use in cervical fusion or Anterior Cervical implants. FIG. 19 shows a perspective view of one embodiment of the interbody spinal implant 301 especially well adapted for use in laterally placed lumbar implants.

Figure 5A:
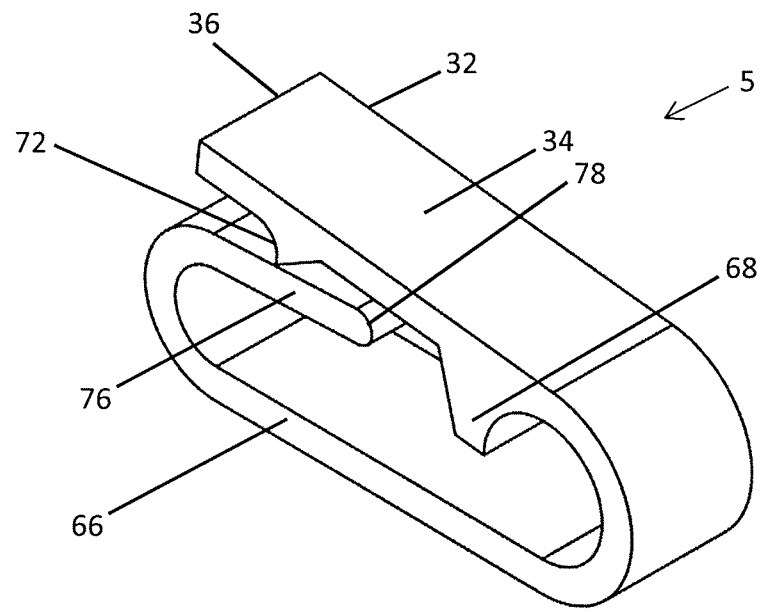
FIG. 5A shows a perspective view of an embodiment of a self-deploying anchor in a retracted condition.
Figure 5B:
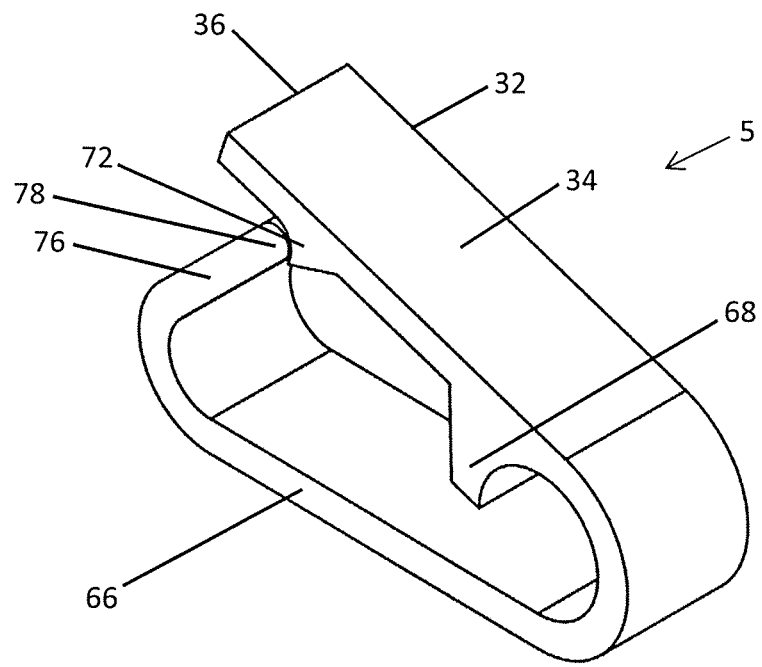
FIG. 5B shows a perspective view of the embodiment depicted in FIG. 5A with the self-deploying anchor in a deployed condition.

The anchor or anchors 5 may be of any suitable shape or configuration as long as the anchors 5 are capable of transitioning from a retracted position to a deployed position. The self-deploying anchor 5 preferably includes at least an expulsion tab 32, an integration surface 34, and a bone-engaging tip 36. The expulsion tab 32 and bone-engaging tip 36 may be of any suitable length, width, thickness, and shape. FIGS. 5A and 5B depict a substantially rectangular expulsion tab 32 where the length of the expulsion tab 32 is greater than the width of the expulsion tab 32, which is greater than the thickness of the expulsion tab 32. The embodiment depicted in FIGS. 5A and 5B also provides a substantially rectangular bone-engaging tip 36. It is envisioned, however, that the bone-engaging tip 36 may be blunt, curved, beveled, or the like. The integration surface 34 and bone-engaging tip 36 contact and may penetrate the vertebral endplate(s) 25 when deployed to prevent movement and expulsion of the implant 1, 101, 101a, 201, and 301 after implantation.

By way of example only, FIGS. 4A, 4B, 5A, and 5B depict one suitable type of anchor 5 having a paper clip shape. The self-deploying anchor 5 may include an expulsion tab 32 having an integration surface 34 and an interior surface 38 opposite the integration surface 34. The anchor 5 may further include a bone-engaging tip 36 and a connecting end opposite the bone-engaging tip 36. When in a retracted condition (e.g., FIGS. 4A and 5A), the integration surface 34 of the expulsion tab 32 may be below or substantially coplanar with the top surface 10, 110, 110a, 210, and 310, bottom surface 20, 120, 120a, 220, and 320, or both surfaces of the implant 1, 101, 101a, 201, and 301. Preferably, substantially all or the entire expulsion tab 32 (and the remainder of the anchor 5) is housed within the body of the implant 1, 101, 101a, 201, and 301 prior to deployment. After implantation (e.g., once the implant 1, 101, 101a, 201, and 301 reaches about body temperature), the self-deploying anchors 5 may expand to a deployed position where the expulsion tab 32 and bone-engaging tip 36 extend outward and beyond the top surface 10, 110, 110a, 210, and 310, bottom surface 20, 120, 120a, 220, and 320, or both surfaces of the implant 1, 101, 101a, 201, and 301 (e.g., FIGS. 4B and 5B). The remainder of the anchor 5 may remain housed within the body of the implant 1, 101, 101a, 201, and 301.

Figure 6A:
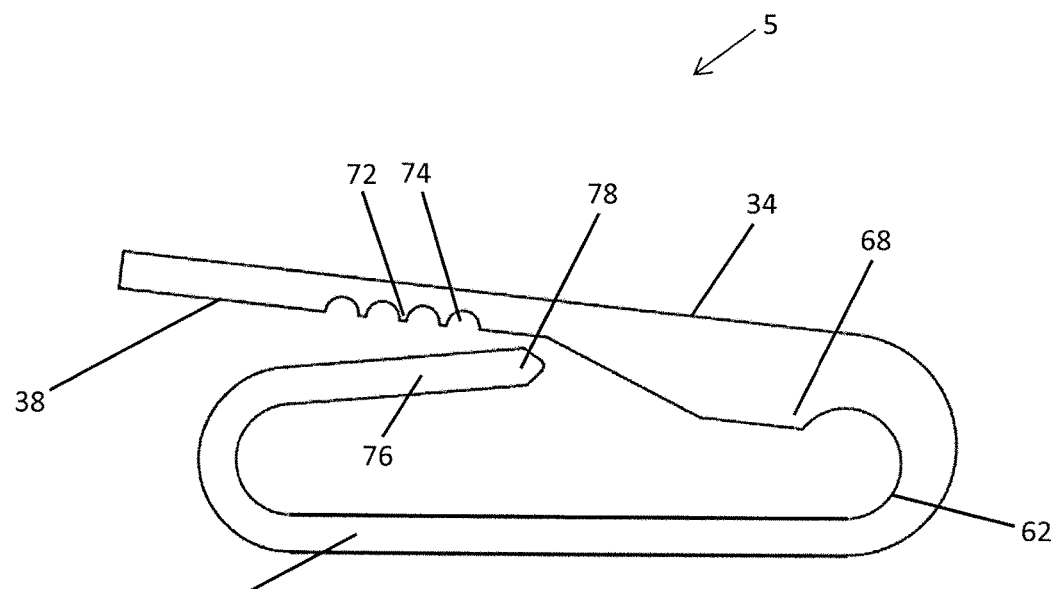
FIG. 6A shows a side view of an embodiment of a self-deploying anchor with a ratchet locking mechanism in a retracted condition.
Figure 6B:
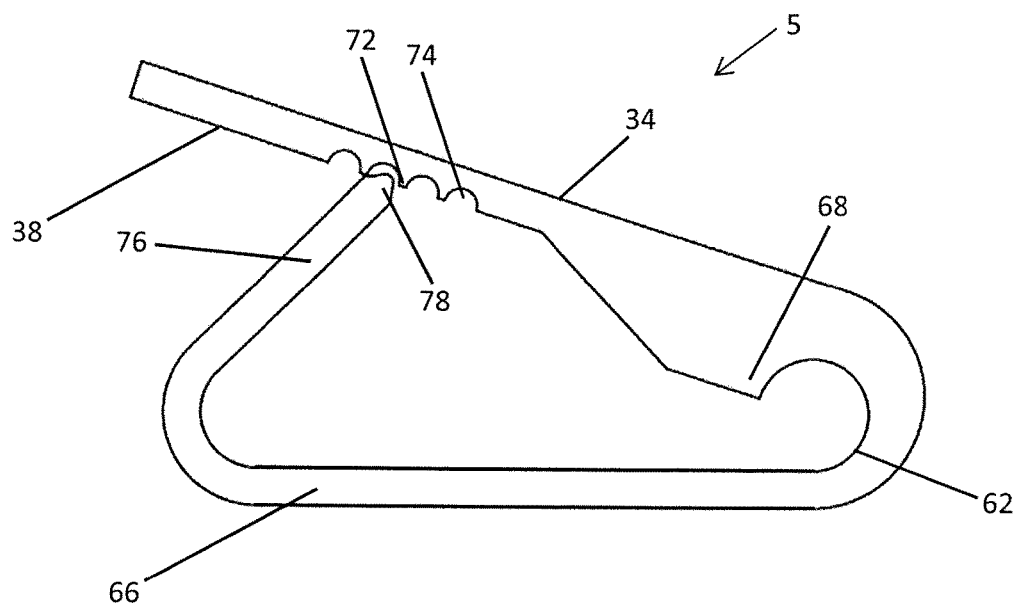
FIG. 6B shows a side view of the embodiment depicted in FIG. 6A with the self-deploying anchor in a deployed condition.
Figure 7A:
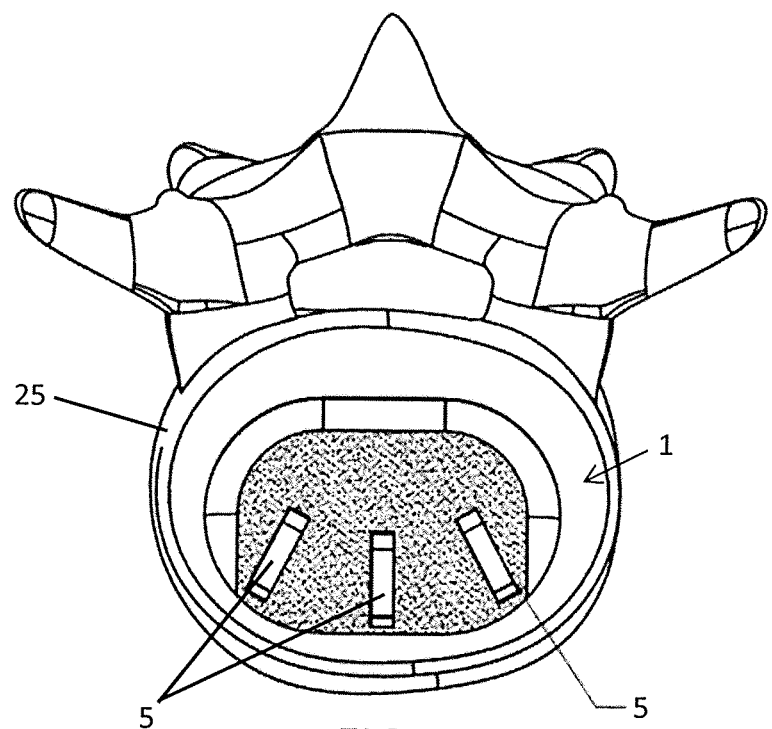
FIG. 7A shows a top view of an embodiment of the interbody spinal implant having a solid body and three self-deploying anchors positioned on a vertebral endplate.
Figure 7B:
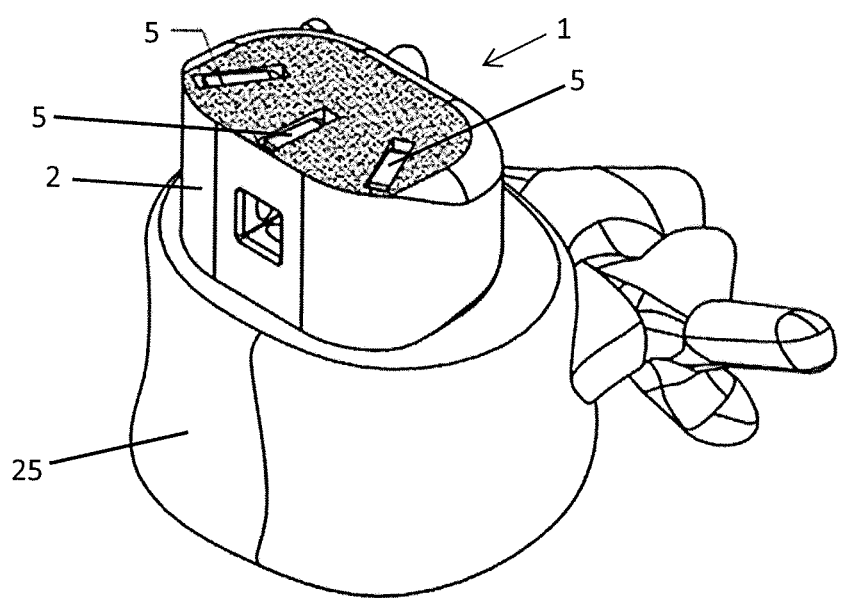
FIG. 7B shows a perspective view of the embodiment of the interbody spinal implant illustrated in FIG. 7A.
Figure 8A:
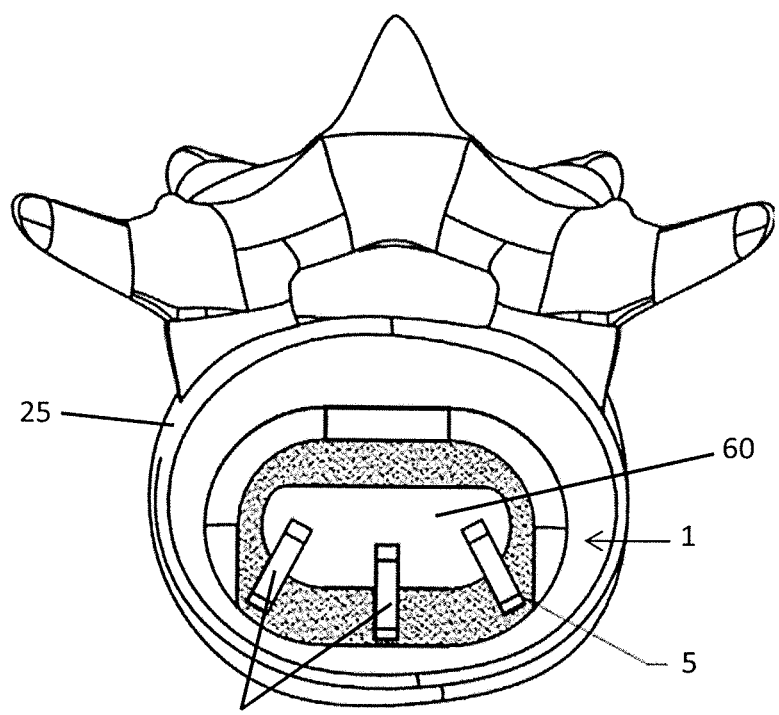
FIG. 8A shows a top view of an embodiment of the interbody spinal implant having a single vertical aperture and substantially hollow center and three self-deploying anchors positioned on a vertebral endplate.
Figure 8B:
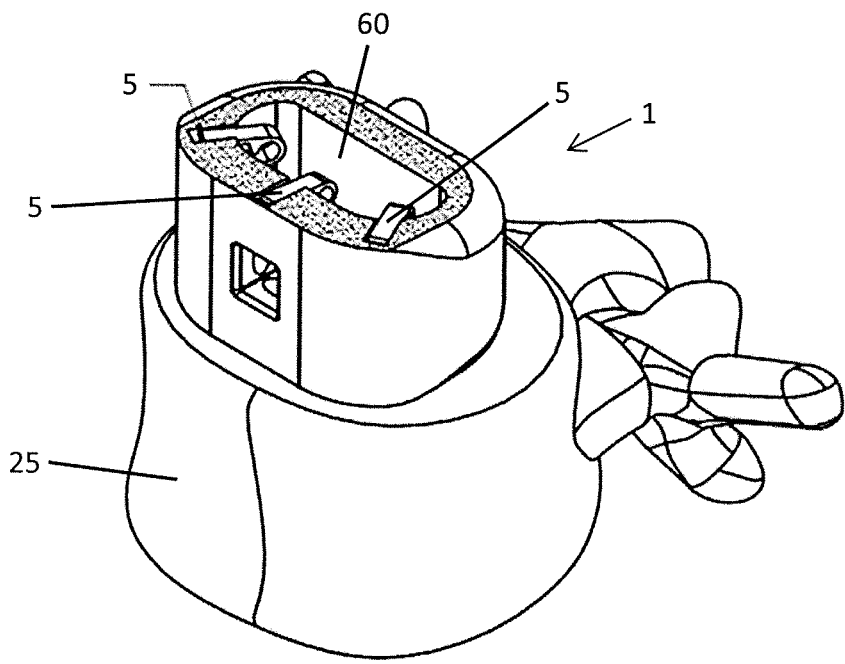
FIG. 8B shows a perspective view of the embodiment of the interbody spinal implant illustrated in FIG. 8A.

The self-deploying anchor 5 may contain a locking mechanism, for example, which engages the expulsion tab 32 and firmly holds the bone-engaging tip 36 in position. By way of example, the anchor 5 may include a locking bar 76 to lock or maintain the anchor 5 in the deployed position after implantation. The locking bar 76 may include a locking tip 78 and a connecting end opposite the locking tip 78. The interior surface 38 of the expulsion tab 32 may include a protrusion 72 which engages the locking tip 78 of the locking bar 76 and prevents a deployed anchor 5 from returning to a retracted position (e.g., FIG. 5B). The locking bar 76 may be of any suitable length, width, thickness, and shape. Preferably, the locking bar 76 is of a suitable size and shape to engage and maintain the expulsion tab 32 in a deployed configuration. FIGS. 5A and 5B depict a substantially rectangular locking bar 76 where the length of the locking bar 76 is greater than the width of the locking bar 76, which is greater than the thickness of the locking bar 76. The width of the locking bar 76 may be the same as or different from the width of the expulsion tab 32. The embodiment depicted in FIGS. 5A and 5B provides a curved locking tip 78 for the locking bar 76, but the locking tip 78 of the locking bar 76 may be blunt, rectangular, beveled, or the like. In another embodiment shown in FIGS. 6A and 6B, the interior surface 38 of the expulsion tab 32 may include a ratchet system 74 having a plurality of protrusions 72 each separated by a recess or indentation where the locking tip 78 enters one recess and the protrusion 72 adjacent to the locking tip 78 stops the anchor 5 from returning to a retracted state once the anchor 5 is deployed.

Each portion of the anchor 5 may be coupled together in any suitable manner and configuration. For example, a connecting piece 66 having a first and second end may connect the expulsion tab 32 and the locking bar 76. The connecting end of the expulsion tab 32 may be coupled to the first end of the connecting piece 66 by a first arcuate member (e.g., a first semi-circular piece) forming a connection bore 62. Similarly, the connecting end of the locking bar 76 may be coupled to the second end of the connecting piece 66 by a second arcuate member (e.g., a second semi-circular piece). Each piece of the anchor 5 may be directly connected together or may be coupled together through one or more intervening elements. All portions of the anchor 5 may be formed from a single piece of material (e.g., nitinol) or one or more portions of the anchor 5 may be connected together via soldering, welding, or the like (e.g., portions of the anchor 5 other than the expulsion tab 32 may be made from non-temperature-sensitive/shape memory materials known in the art).

Figure 11A:
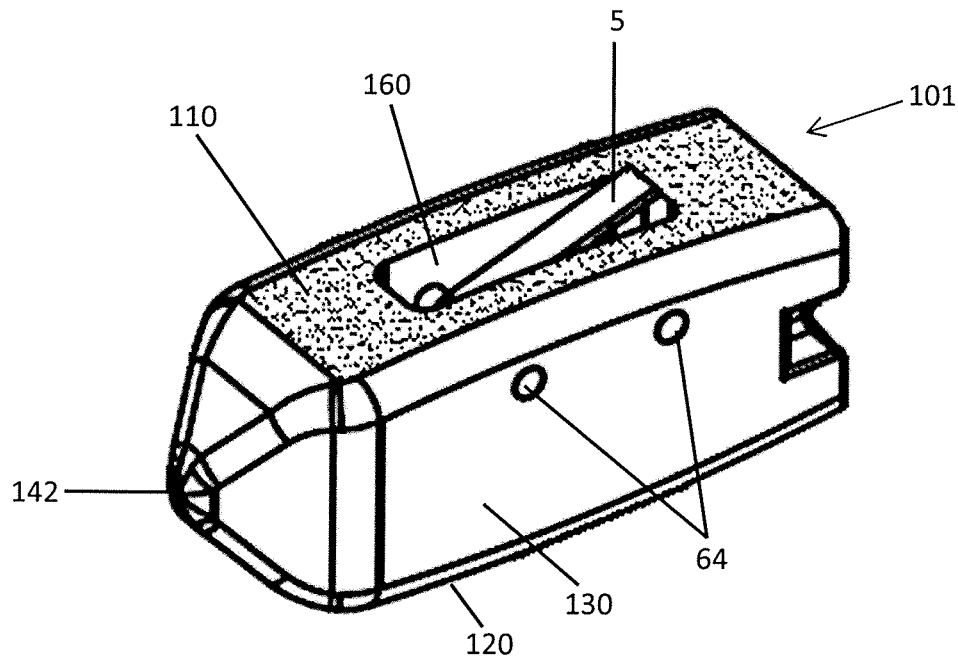
FIG. 11A shows a perspective view of an embodiment of the interbody spinal implant having self-deploying anchors in a deployed condition.

The anchors 5 may be affixed to the implant 1, 101, 101a, 201, and 301 using any suitable attachment mechanisms. For example, the anchors 5 or a portion of the anchors 5 may be mechanically affixed to (e.g., using a pin 64), embedded in, welded to, or otherwise adhered to the implant 1, 101, 101a, 201, and 301. In an exemplary embodiment, the anchors 5 are affixed to the implant 1, 101, 101a, 201, and 301 with at least one pin 64, bolt, shaft, or the like. For example, the pin 64 may extend through the connection bore 62. To enhance mechanical connection, the internal surface of the connection bore 62 or the interior surface 38 of the expulsion tab 32 may contain protrusions, ridges, grooves, or other friction-enhancing surfaces to maintain the position of the pin 64. For example, the anchor 5 may further include a tab 68, for example, to improve the surface contact of the pin 64 with the anchor 5. The pin 64 may be secured to the implant 1, 101, 101a, 201, and 301 in any suitable manner, for example, into the lateral sides 30, 130, 130a, 230, and 330 of the implant 1, 101, 101a, 201, and 301 (e.g., FIG. 11A); the anterior 40, 140, 140a, 240, and 340 and posterior 50, 150, 150a, 250, and 350 portions of the implant 1, 101, 101a, 201, and 301; or any other suitable location. The anchors 5 may optionally include a second pin 64, bolt, shaft, or the like, which extends through an opening formed by the second arcuate member. FIG. 11A depicts an embodiment with two pins 64 in each of the connection bore 62 and the second arcuate member connecting the locking bar 76.

Figure 11B:
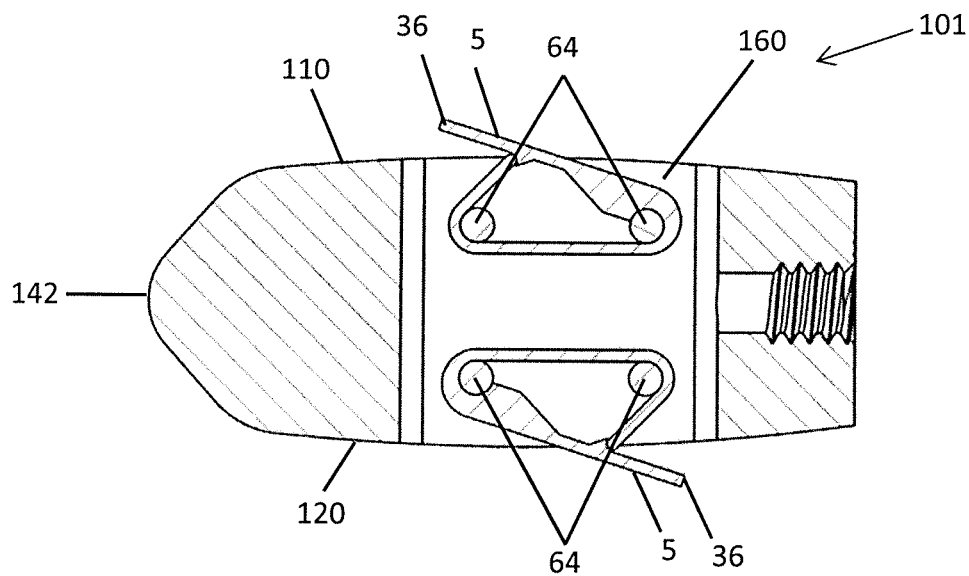
FIG. 11B shows a side view of the embodiment of the interbody spinal implant illustrated in FIG. 11A.

The top 10, 110, 110a, 210, and 310 and bottom 20, 120, 120a, 220, and 320 surfaces of the implant 1, 101, 101a, 201, and 301 may include any suitable number and placement of anchors 5 in order to minimize or resist expulsion. For example, one, two, three, or more anchors 5 may be positioned on each of the top 10, 110, 110a, 210, and 310 and bottom 20, 120, 120a, 220, and 320 surfaces of the implant 1, 101, 101a, 201, and 301. In one embodiment, the implant 101 includes at least one self-deploying anchor 5 (FIGS. 11A and 11B) on each of the top 110 and bottom 120 surfaces. In another embodiment, the implant 101 includes at least two self-deploying anchors 5 on the top surface 110, the bottom 120 surface, or both surfaces (FIGS. 9A and 9B). In another embodiment, the implant 1 includes at least three self-deploying anchors 5 on the top surface 10, the bottom 20 surface, or both surfaces (FIGS. 1A and 1B).

The bone-engaging tips 36 may be oriented in any suitable direction, preferably, in the direction or directions necessary to prevent expulsion of the implant 1, 101, 101a, 201, and 301. The anchors 5 may be positioned in the same or different directions. In one embodiment, the bone-engaging tips 36 are each oriented substantially toward the anterior portion 40 of the implant 1 (FIGS. 1A and 1B). In another embodiment, at least two self-deploying anchors 5 and the bone-engaging tips 36 are oriented in opposite directions. For example, the bone-engaging tip 36 of the first self-deploying anchor 5 may be oriented substantially toward the anterior portion 140 of the implant and the bone-engaging tip 36 of the second self-deploying anchor 5 may be oriented substantially toward the posterior portion 150 of the implant 101 (FIGS. 9A and 9B).

Figure 12A:
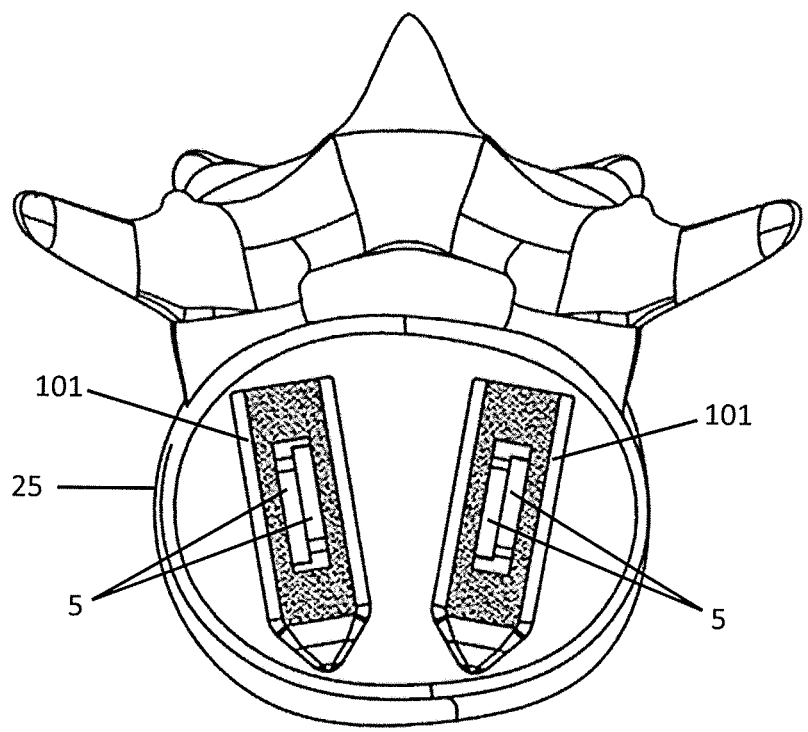
FIG. 12A shows a top view of an embodiment of two interbody spinal implants each having two self-deploying anchors positioned in opposite directions positioned on a vertebral endplate.
Figure 12B:
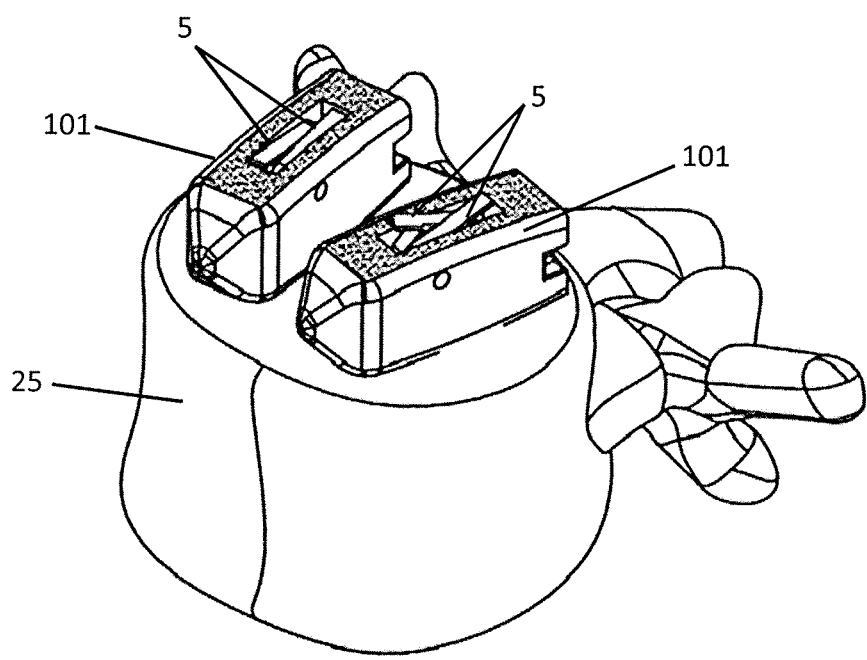
FIG. 12B shows a perspective view of the embodiment of the two interbody spinal implants illustrated in FIG. 12A.
Figure 16A:
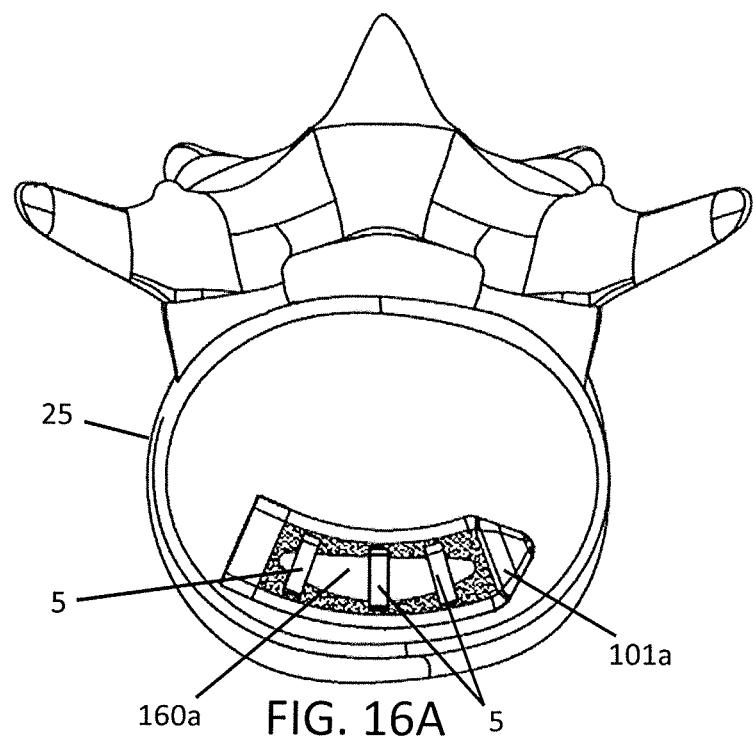
FIG. 16A shows a top view of an embodiment of the interbody spinal implant having a single vertical aperture and substantially hollow center and three self-deploying anchors positioned on a vertebral endplate.
Figure 16B:
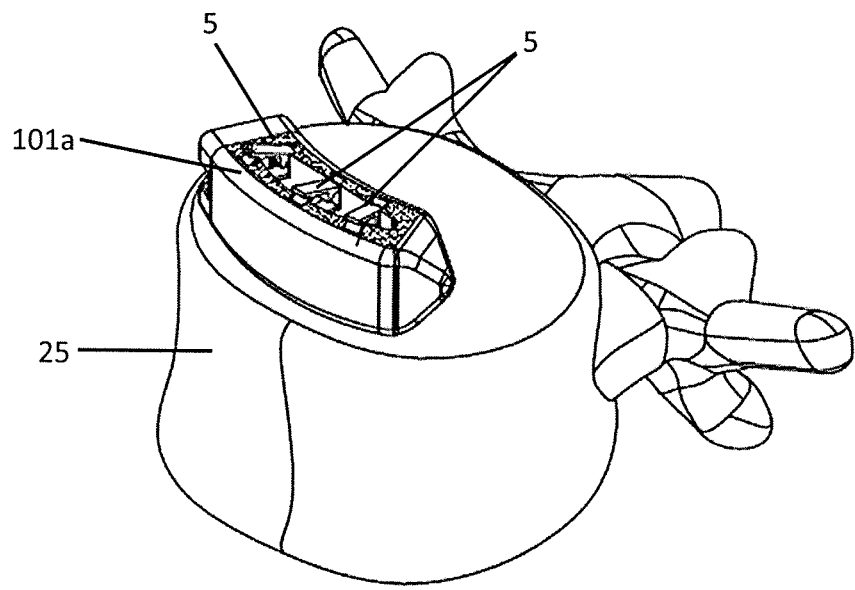
FIG. 16B shows a perspective view of the embodiment of the interbody spinal implant illustrated in FIG. 16A in a deployed condition.

The anchors 5 may be positioned at any suitable point or location along the top 10, 110, 110a, 210, and 310 and bottom 20, 120, 120a, 220, and 320 surfaces of the implant 1, 101, 101a, 201, and 301. For example, the anchors 5 may be centrally positioned on the top surface 10, 110, 110a, 210, and 310, the bottom surface 20, 120, 120a, 220, and 320, or both surfaces (e.g., FIGS. 12A and 12B). The anchors 5 may be positioned proximate the anterior portion 40 of the implant 1 (e.g., FIGS. 1A and 1B). The anchors 5 may be positioned across the entire face of the top surface, 10, 110, 110a, 210, and 310, the bottom surface 20, 120, 120a, 220, and 320, or both surfaces of the implant 1, 101, 101a, 201, and 301 (e.g., FIGS. 16A and 16B).

The self-deploying anchors 5 may function to allow for smaller and more easily implanted implant bodies that resists expulsion (e.g., from biological loading from the posterior to anterior disc space) due to the location and orientation of the one or more anchors 5.

Implants

The spinal implant 1, 101, 101a, 201, and 301 includes a top surface 10, 110, 110a, 210, and 310, a bottom surface 20, 120, 120a, 220, and 320, opposing lateral sides 30, 130, 130a, 230, and 330, and opposing anterior 40, 140, 140a, 240, and 340 and posterior 50, 150, 150a, 250, and 350 portions. The implant 1, 101, 101a, 201, and 301 may be of any suitable shape. For example, the body of the implant 1, 101, 101a, 201, and 301 may have a generally oval shape, a generally rectangular shape, a generally curved shape, or any other shape described or exemplified in this specification. Certain embodiments of the interbody implant 1 have a generally oval-shaped transverse cross-sectional area (e.g., FIG. 1A), which may be suitable for ALIF. The implant 101 may have a generally rectangular transverse cross-sectional area (e.g., FIG. 10A) suitable for PLIF. The implant 101a may have a generally curved shape (e.g., FIG. 13A) suitable for TLIF fusion. The implant 201 may be generally circular in shape (e.g., FIG. 17) suitable for cervical fusion. The implant 301 may be generally rectangular in shape (e.g., FIG. 19) suitable for lateral lumbar insertion. The implant 1, 101, 101a, 201, and 301 may be shaped to reduce the risk of subsidence, and improve stability, by maximizing contact with the apophyseal rim of vertebral endplates 25. Embodiments may be provided in a variety of anatomical footprints and sizes.

The implant 1, 101, 101a, 201, and 301 may comprise a solid body 2 (e.g., FIGS. 7A, 7B, 15A, and 15B). Implants 1, 101, 101a, 201, and 301 having a solid body 2 contain no apertures or openings extending through the implant 1, 101, 101a, 201, and 301 (e.g., in the vertical or transverse directions). The implants 1, 101, 101a, 201, and 301 may contain openings (e.g., an opening 90), however, in one or more surfaces of the implant 1, 101, 101a, 201, and 301, for example, for manipulation of tools and the like. The solid body implants 1, 101, 101a, 201, and 301 may be formed from a single material or more than one material (e.g., a composite). In the case of a solid body implant 1, 101, 101a, 201, and 301, the one or more anchors 5 may be positioned at any suitable location on the top 10, 110, 110a, 210, and 310 and bottom 20, 120, 120a, 220, and 320 surfaces.

The implant 1, 101, 101a, 201, and 301 comprise one or more apertures (e.g., FIGS. 2A, 2B, 8A, and 8B). For example, the implant 1, 101, 101a, 201, and 301 may comprise one or more apertures which extend through the body of the implant 1, 101, 101a, 201, and 301. The implant 1, 101, 101a, 201, and 301 may include one or more vertical apertures 60, 160, 160a, 260, and 360 extending through the main body of the implant 1, 101, 101a, 201, and 301, respectively. In an exemplary embodiment, the implant 1, 101, 101a, 201, and 301 includes a single vertical aperture 60, 160, 160a, 260, and 360 which (a) extends from the top surface 10, 110, 110a, 210, and 310 to the bottom surface 20, 120, 120a, 220, and 320, (b) has a size and shape predetermined to maximize the surface area of the top surface 10, 110, 110a, 210, and 310 and the bottom surface 20, 120, 120a, 220, and 320 available proximate the anterior 40, 140, 140a, 240, and 340 and posterior 50, 150, 150a, 250, and 350 portions while maximizing both radiographic visualization and access to the substantially hollow center, and optionally (c) defines a transverse rim 100.

Figure 3A:
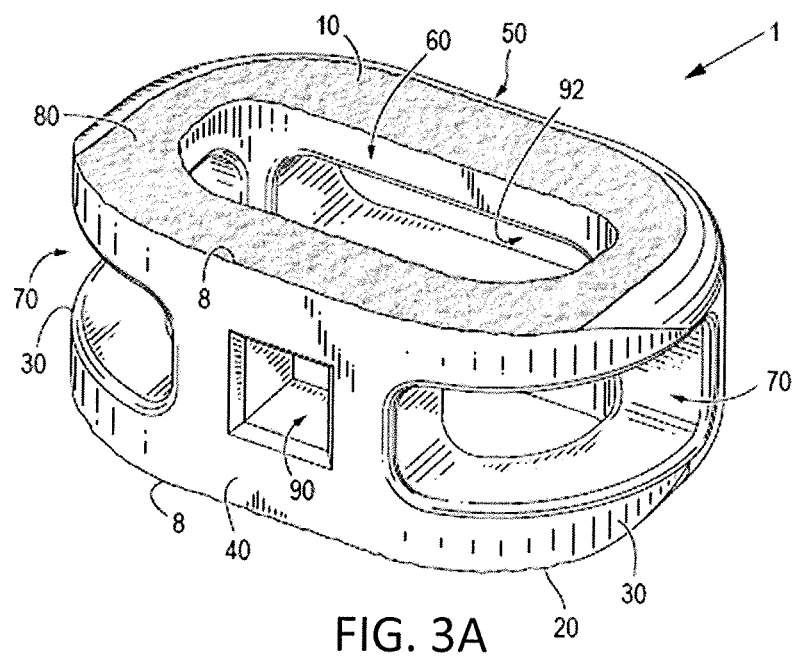
FIG. 3A shows a perspective view of an embodiment of the interbody spinal implant having a generally oval shape and roughened surface topography on the top surface.
Figure 3B:
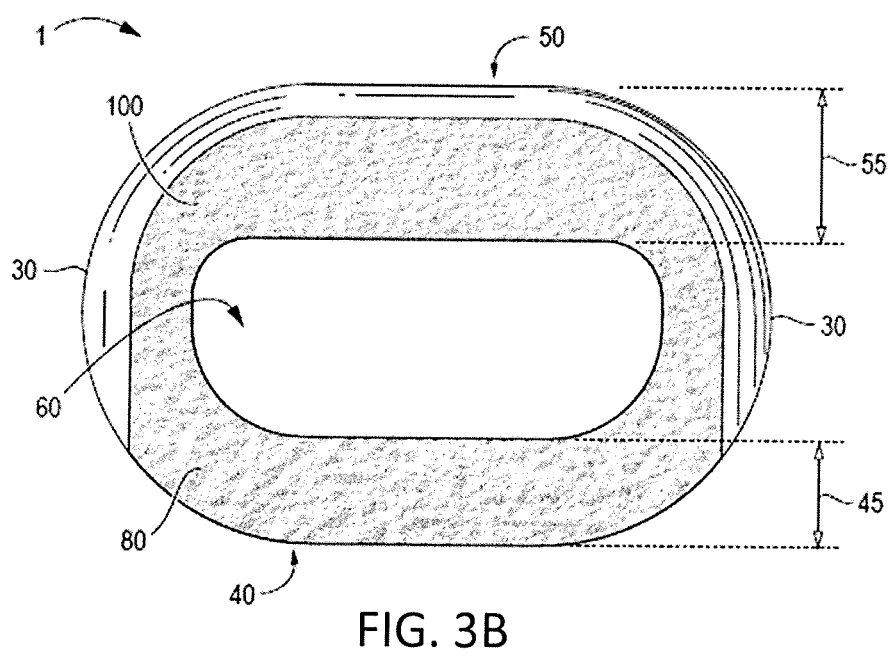
FIG. 3B shows a top view of the embodiment of the interbody spinal implant illustrated in FIG. 3A.
Figure 4A:
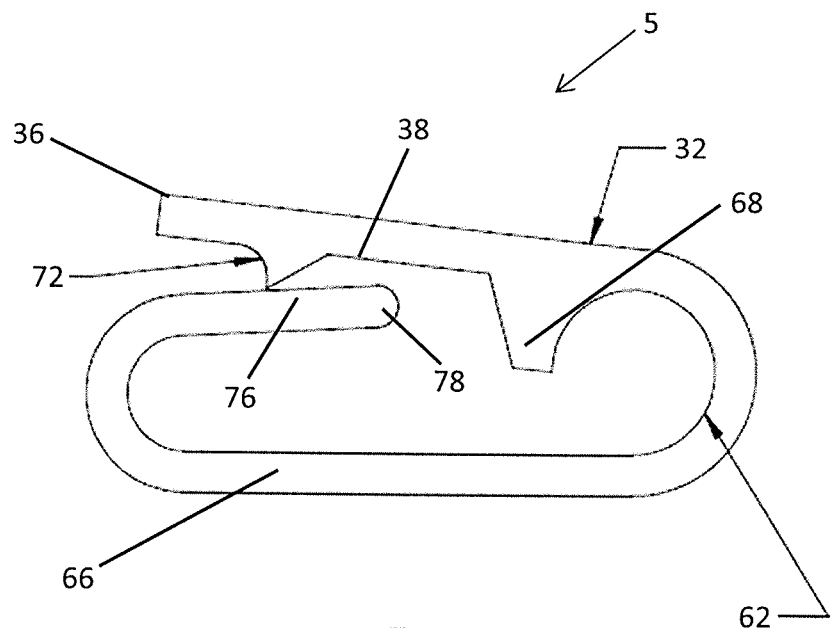
FIG. 4A shows a side view of an embodiment of a self-deploying anchor in a retracted condition.
Figure 4B:
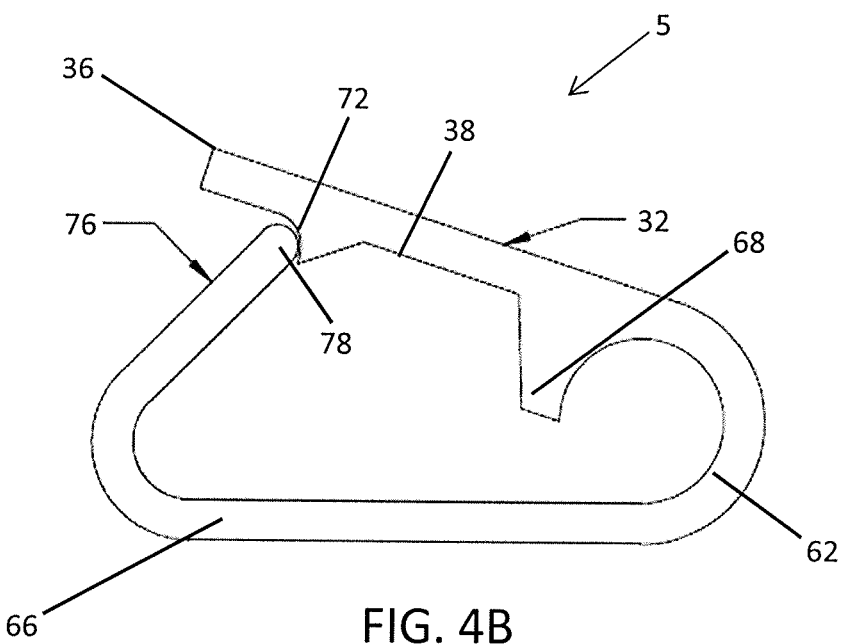
FIG. 4B shows a side view of the embodiment depicted in FIG. 4A with the self-deploying anchor in a deployed condition.

The vertical aperture 60 may define a transverse rim 100 having a greater posterior portion thickness 55 than an anterior portion thickness 45 (see e.g., FIGS. 3A and 3B). In at least one embodiment, the opposing lateral sides 30 and the anterior portion 40 have a rim thickness 45 of about 5 mm, while the posterior portion 50 has a rim thickness 55 of about 7 mm. Thus, the rim posterior portion thickness 55 may allow for better stress sharing between the implant 1 and the adjacent vertebral endplates 25 and helps to compensate for the weaker posterior endplate bone. In some aspects, the transverse rim 100 has a generally large surface area and contacts the vertebral endplate 25. The transverse rim 100 may act to better distribute contact stresses upon the implant 1, and hence minimize the risk of subsidence while maximizing contact with the apophyseal supportive bone. It is also possible for the transverse rim 100 to have a substantially constant thickness (e.g., for the anterior portion thickness 45 to be substantially the same as the posterior portion thickness 55) or for the posterior portion 50 to have a rim thickness 55 less than that of the opposing lateral sides 30 and the anterior portion 40.

FIG. 13A illustrates a perspective view of the implant 101a with a curved transverse rim 200a. The width of the transverse rim 200a is 9 mm in the regions adjacent the anterior 140a and posterior 150a portions. That width gradually increases to 11 mm, however, near the center of the transverse rim 200a. The additional real estate provided by the transverse rim 200a (relative to the transverse rim 200) allows the shape of the vertical aperture 160a to change, in cross section, from approximating a football to approximating a boomerang. Maintaining the thickness of the transverse rim 200a on either side of the vertical aperture 160a adjacent the center of the vertical aperture 160a at about 2 mm, the center of the vertical aperture 160a, which defines the maximum width of the vertical aperture 160a, is increased (from 5 mm for the implant 101) to about 7 mm.

Certain embodiments of the interbody implant 1, 101, 101a, 201, and 301 are substantially hollow. Substantially hollow, as used in this document, means at least about 33% of the interior volume of the interbody spinal implant 1, 101, 101a, 201, and 301 is vacant. The substantially hollow portion may be filled, for example, with cancellous autograft bone, allograft bone, demineralized bone matrix (DBM), porous synthetic bone graft substitute, bone morphogenic protein (BMP), or combinations of those materials.

The implant 1, 101, 101a, 201, and 301 may further comprise one or more transverse apertures 70, 170, 170a, and 270. The transverse aperture 70, 170, 170a, and 270 may extend the entire transverse length of the body of the implant 1, 101, 101a, 201, and 301. The transverse aperture 70, 170, 170a, and 270 may provide improved visibility of the implant 1, 101, 101a, 201, and 301 during surgical procedures to ensure proper implant placement and seating, and may also improve post-operative assessment of implant fusion. The transverse aperture 70, 170, 170a, and 270 may be broken into two, separate sections by an intermediate wall. Suitable shapes and dimensions for the transverse aperture 70, 170, 170a, and 270 may be selected by one of ordinary skill in the art. In particular, all edges of the transverse aperture 70, 170, 170a, and 270 may be rounded, smooth, or both. The intermediate wall may be made of the same material as the remainder of the body of the implant 1, 101, 101a, 201, and 301 (e.g., titanium), or it may be made of another material (e.g., plastic). The intermediate wall may offer one or more of several advantages, including reinforcement of the implant 1, 101, 101a, 201, and 301 and improved bone graft containment.

Figure 14:
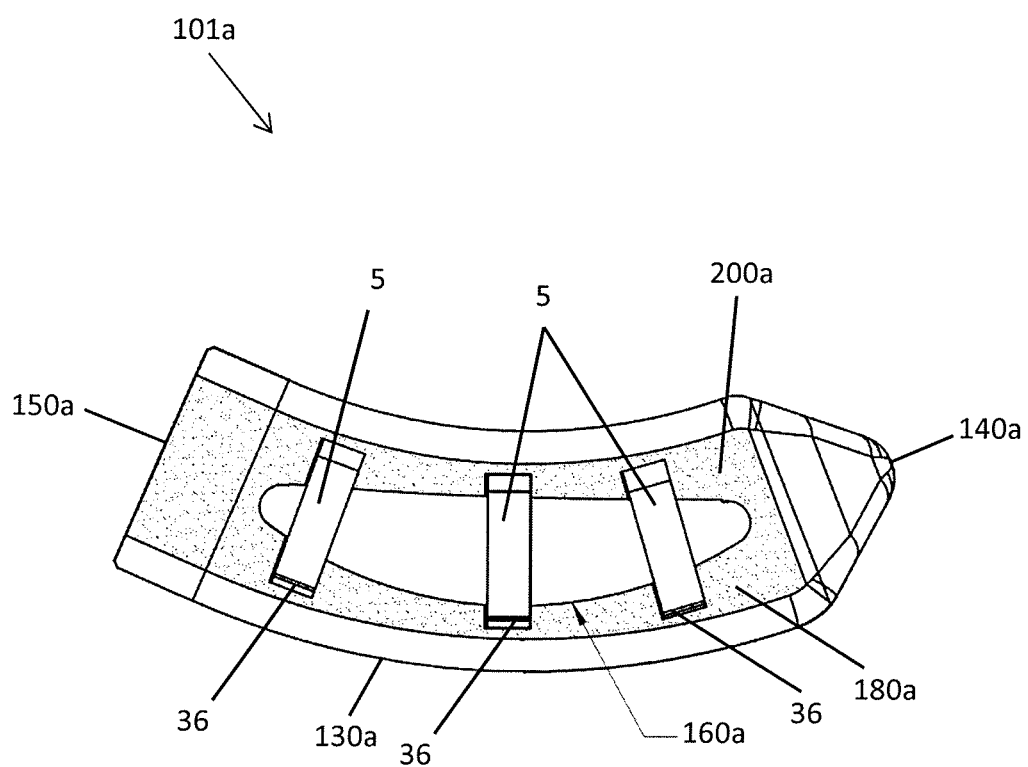
FIG. 14 shows a top view of an embodiment of the interbody spinal implant having a single vertical aperture and substantially hollow center and three self-deploying anchors.
Figure 15A:
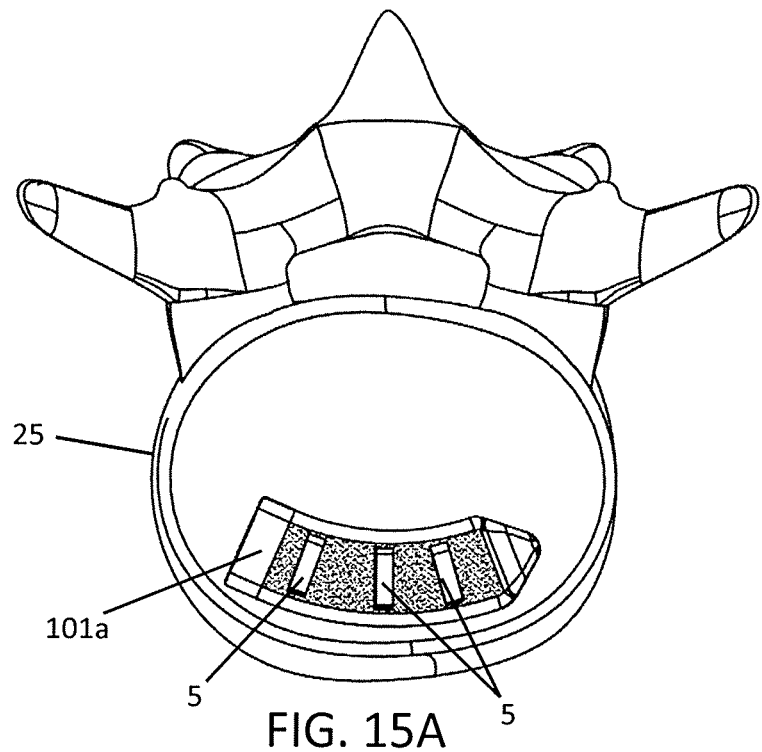
FIG. 15A shows a top view of an embodiment of the interbody spinal implant having a solid body and three self-deploying anchors positioned on a vertebral endplate.
Figure 15B:
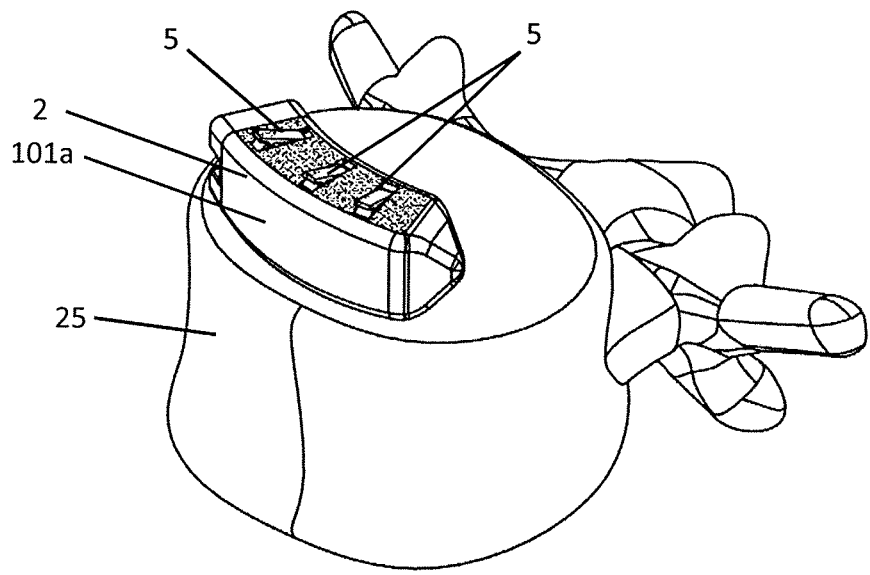
FIG. 15B shows a perspective view of the embodiment of the interbody spinal implant illustrated in FIG. 15A in a deployed condition.

In the case of an implant 1, 101, 101a, 201, and 301 comprising one or more apertures (e.g., a single vertical aperture 60, 160, 160a, 260, and 360), the one or more anchors 5 may be positioned at any suitable location on the top 10, 110, 110a, 210, and 310 and bottom 20, 120, 120a, 220, and 320 surfaces. For example, the anchors 5 may be positioned on the transverse rim 100. The anchors 5 may also span, traverse, or be positioned in or over open areas as long as the anchors 5 are adequately secured to the implant 1, 101, 101a, 201, and 301 (e.g., FIG. 14).

Figure 18:
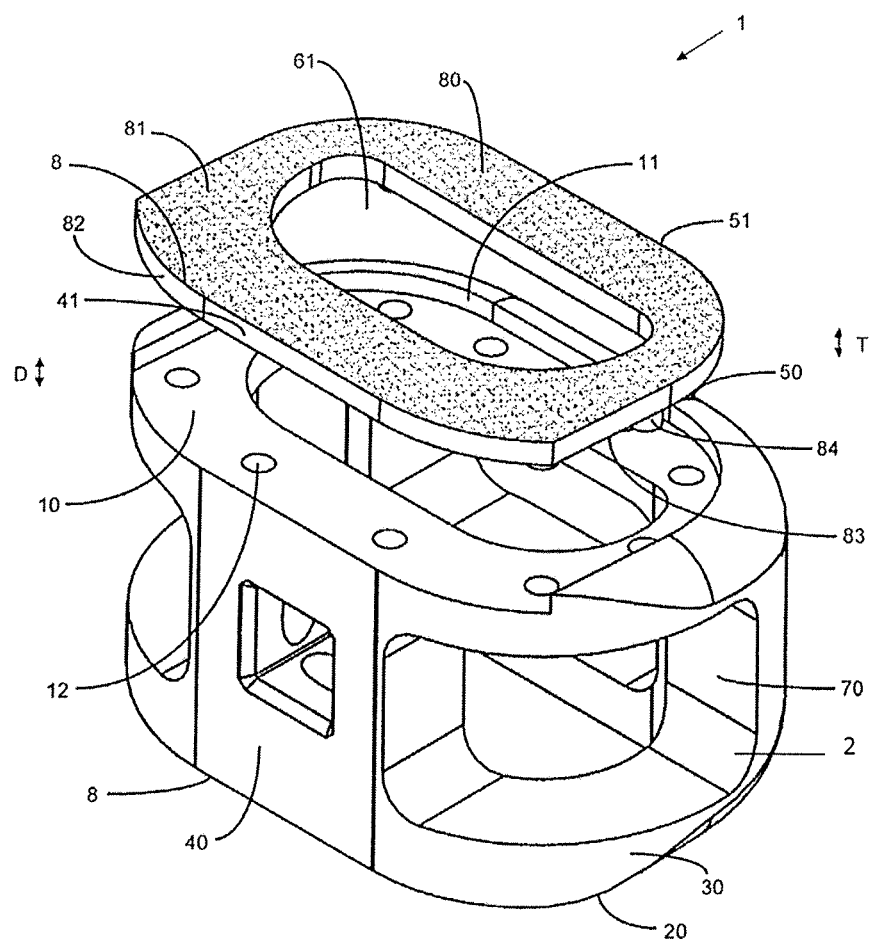
FIG. 18 shows an exploded view of a generally oval-shaped implant with an integration plate.

The implant 1, 101, 101a, 201, and 301 may be formed from a single material or may be formed as a composite made from more than one type of material. As depicted in FIGS. 18 and 19, a composite implant 1, 101, 101a, 201, and 301 may comprise one or two integration plates 82, 382, for example. The implant 1, 101, 101a, 201, and 301 may include a first integration plate 82, 382 affixed to the top surface 10, 310 of the body 2 and an optional second integration plate 82, 382 (not shown) affixed to the bottom surface 20, 320 of the body 2. The first integration plate 82, 382 and optional second integration plate 82, 382 each have a top surface 81, 381, a bottom surface 83, 383, opposing lateral sides, opposing anterior portion 41, 341 and posterior portion 51, 351, and a single vertical aperture 61, 361 extending from the top surface 81, 381 to the bottom surface 83, 383 and aligning with the single vertical aperture 60, 360 of the body 2, when present. In the case of a composite implant 1, 101, 101a, 201, and 301 with one or more integration plates 82, 382, the top surface 81, 381 would be the outer surface or integration surface of the implant 1, 101, 101a, 201, and 301. Preferably, the integration plate 82, 382 should be designed to be compatibly shaped and match the dimensions of the body 2 of the implant 1, 101, 101a, 201, and 301. In a composite implant 1, 101, 101a, 201, and 301, the components may be permanently assembled together.

The integration plate 82, 382 may be attached or affixed to the main body 2 of the implant 1, 101, 101a, 201, and 301 using any suitable mechanisms known in the art, for example, a reciprocal connector structure (such as a plurality of posts 84, 384 and holes 12, 312 depicted in FIGS. 18 and 19), fasteners (e.g., a pin, screw, bolt, rod, anchor, snap, clasp, clip, clamp, or rivet), compatibly shaped joints, compatibly shaped undercuts, and/or other suitable connectors having different shapes, sizes, and configurations. An adhesive (e.g., cement, glue, polymer, epoxy, solder, and weld) may also be used to further strengthen any connections described in this specification. The top surface 10, 310 or bottom surface 20, 320 may be recessed at a depth D to allow a thickness T of the integration plate 82, 382 to recess within and form a substantially contiguous outer surface. Recessing the top surface 10, 310 or bottom surface 20, 320 exposes a ridge 11, 311 against which the anterior portion 41, 341, posterior portion 51, 251 or lateral side of the integration plate 82, 382 may be seated when brought together with the implant 1, 301.

Figure 10A:
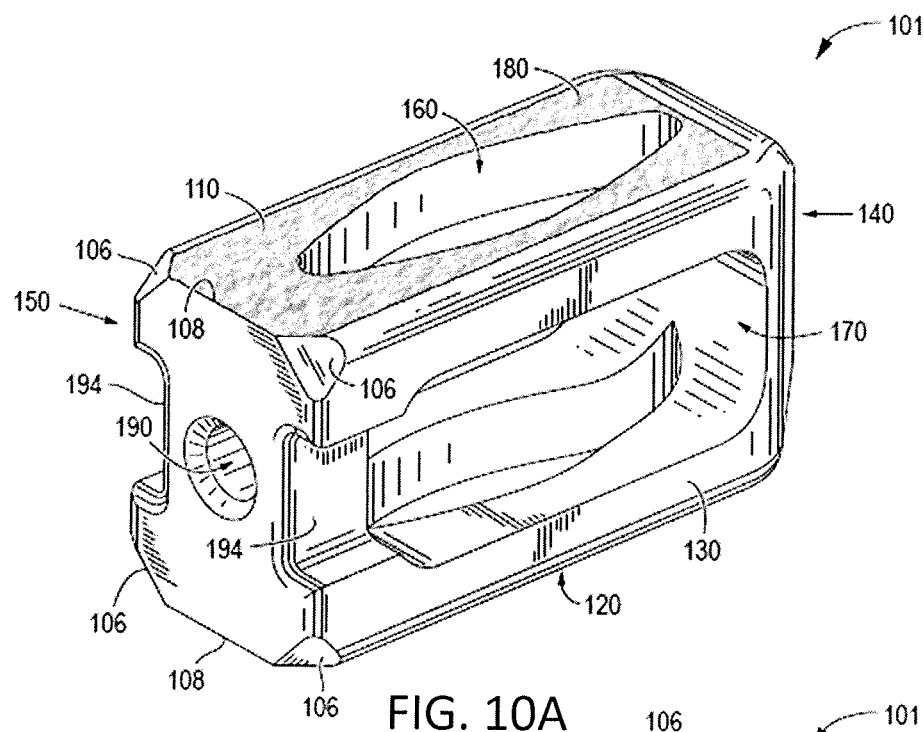
FIG. 10A shows a perspective view from the front of an embodiment of the interbody spinal implant according to the present invention.
Figure 10B:
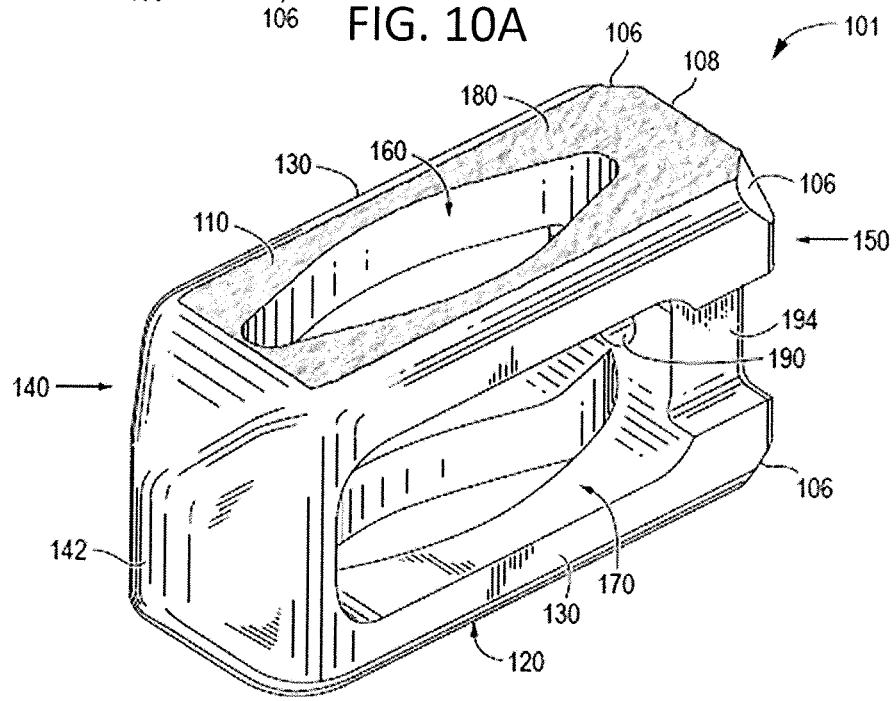
FIG. 10B shows a perspective view from the rear of the embodiment of the interbody spinal implant illustrated in FIG. 10A.

In addition, the implant 1, 101, 101a, 201, and 301 may comprise some or all of the following implant features alone or in combination. The implant 1, 101, 101a, 201, and 301 may include smooth, rounded, or both smooth and rounded lateral sides 30 and posterior-lateral corners. As best shown in FIG. 10B and FIGS. 13A and 13B, the anterior portion 140, 140a may have a tapered nose 142, 142a to facilitate insertion of the implant 101, 101a. To further facilitate insertion, the implant 101 may have chamfers 106 at the corners of its posterior portion 150. The chamfers 106 prevent the implant 101 from catching upon insertion, risking potential damage such as severed nerves, while still permitting the implant 101 to have a sharp edge 108.

The implant 1, 101, 101a, 201, and 301 may include an opening 90, 190, 190a, 290, 390, for example, in the anterior portion 40, 140, 140a, 240, and 340. The posterior portion 50, 150, 150a, 250, and 350 may have a similarly shaped opening 90, 190, 190a, 290, 390 (not shown). In some aspects, only the anterior portion 40, 140, 140a, 240, and 340 has the opening 90, 190, 190a, 290, 390 while the posterior portion 50 has an alternative opening 92 (which may have a size and shape different from the opening 90, 190, 190a, 290, 390).

The opening 90, 190, 190a, 290, 390 has a number of functions. One function is to facilitate manipulation of the implant 1, 101, 101a, 201, and 301 by the caretaker. Thus, the caretaker may insert a surgical tool into the opening 90, 190, 190a, 290, 390 and, through the engagement between the surgical tool and the opening 90, 190, 190a, 290, 390, manipulate the implant 1, 101, 101a, 201, and 301. The opening 90, 190, 190a, 290, 390 may be threaded to enhance the engagement. A suitable surgical tool, such as a distractor (not shown), may be selected by one of ordinary skill in the art.

The implant 101, 101a may also have an Implant Holding Feature (IHF) 194, 194a instead of or in addition to the opening 190. As illustrated in FIGS. 10A and 13A, the IHF 194, 194a is located proximate the opening 190, 190a in the posterior portion 150, 150a. In this particular example, the IHF 194, 194a is a U-shaped notch. Like the opening 190, 190a, the IHF 194, 194a has a number of functions, one of which is to facilitate manipulation of the implant 101 by the caretaker. Other functions of the opening 190, 190a and the IHF 194, 194a are to increase visibility of the implant 101, 101a during surgical procedures and to enhance engagement between bone graft material and adjacent bone.

As illustrated in FIG. 10A, the posterior portion 150 of the implant 101 may be substantially flat. Thus, the posterior portion 150 provides a face that can receive impact from a tool, such as a surgical hammer, to force the implant 101 into position.

The implant 1, 101, 101a, 201, and 301 may be provided with a solid rear wall 242. The rear wall 242 may extend the entire width of the implant body and nearly the entire height of the implant body. Thus, the rear wall 242 can essentially close the anterior portion 40, 140, 140a, 240, and 340 of the implant 1, 101, 101a, 201, and 301. The rear wall 242 may offer one or more of several advantages, including reinforcement of the implant 1, 101, 101a, 201, and 301 and improved bone graft containment. In the cervical application, it may be important to prevent bone graft material from entering the spinal canal.

The implant 1, 101, 101a, 201, and 301 may also have a lordotic angle to facilitate alignment. Depending on the type of implant 1, 101, 101a, 201, and 301, one lateral side 30, 130, 130a, 230, and 330 is preferably generally greater in height than the opposing lateral side 30, 130, 130a, 230, and 330 or the anterior portion 40, 140, 140a, 240, and 340 may be generally greater in height than the opposing posterior portion 50, 150, 150a, 250, and 350. Therefore, the implant 1, 101, 101a, 201, and 301 may better compensate for the generally less supportive bone found in certain regions of the vertebral endplate. As much as seven to fifteen degrees of lordosis (or more) may be built into the implant 1, 101, 101a, 201, and 301 to help restore cervical balance.

To enhance movement resistance and provide additional stability under spinal loads in the body, the implant 1, 101, and 301 may comprise one or more anti-expulsion edges 8, 108, and 308 that tend to "dig" into the end-plates slightly and help to resist expulsion. The anti-expulsion edges 8, 108, and 308 may be present on the top surface 10, 110, and 310; the bottom surface 20, 120, and 320; or both surfaces of the implant 1, 101, and 301 (or the top surface 81 of the integration plate 82 when present). Each anti-expulsion edge 8, 108, and 308 may protrude above the plane of the top surface 10, 110, and 310 or bottom surface 20, 120, and 320, with the amount of protrusion increasing toward the anterior face 40, 140, and 340 and the highest protrusion height at the anterior-most edge of the top surface 10, 110, and 310 or bottom surface 20, 120, and 320.

An anti-expulsion edge 8, 108, and 308 may be oriented toward the anterior portion 40, 140, and 340, or the posterior portion 50, 150, and 350, or either of the opposing lateral sides 30, 130, and 330. The orientation of the anti-expulsion edge 8, 108, and 308 may depend on the intended orientation of the implant 1, 101, and 301 when it has been implanted between vertebrae in the patient.

The implant 1, 101, 101a, 201, and 301 may be composed of any suitable biocompatible material. In an exemplary embodiment, the implant 1, 101, 101a, 201, and 301 is formed of metal. The metal may be coated or not coated. Suitable metals, such as titanium, aluminum, vanadium, tantalum, stainless steel, and alloys thereof, may be selected by one of ordinary skill in the art. In a preferred embodiment, the implant 1, 101, 101a, 201, and 301 includes at least one of titanium, aluminum, and vanadium, without any coatings. In a more preferred embodiment, the implant 1, 101, 101a, 201, and 301 is comprised of titanium or a titanium alloy. An oxide layer may naturally form on a titanium or titanium alloy. Titanium and its alloys are generally preferred for certain embodiments of the present invention due to their acceptable, and desirable, strength and biocompatibility. In this manner, certain embodiments of the present interbody spinal implant 1, 101, 101a, 201, and 301 may have improved structural integrity and may better resist fracture during implantation by impact.

In the case of a composite, the implant 1, 101, 101a, 201, and 301 may further comprise another suitable biocompatible material. For example, in the case of a composite implant 1, 101, 101a, 201, and 301 with one or more integration plates 82, 382, the integration plates 82, 382 may be formed from the metals described above and the body 2 of the implant 1, 101, 101a, 201, and 301 may be formed from a plastic, polymeric, or composite material. For example, suitable polymers may comprise silicones, polyolefins, polyesters, polyethers, polystyrenes, polyurethanes, acrylates, and co-polymers and mixtures thereof. Certain embodiments of the present invention may be comprised of a biocompatible, polymeric matrix reinforced with bioactive fillers, fibers, or both. Certain embodiments of the present invention may be comprised of urethane dimethacrylate (DUDMA)/tri-ethylene glycol dimethacrylate (TEDGMA) blended resin and a plurality of fillers and fibers including bioactive fillers and E-glass fibers. In another embodiment, the body comprises polyetherether-ketone (PEEK), hedrocel, or ultra-high molecular weight polyethylene (UHMWPE). Hedrocel is a composite material composed of carbon and an inert metal, such as tantalum. UHMWPE, also known as high-modulus polyethylene (HMPE) or high-performance polyethylene (HPPE), is a subset of the thermoplastic polyethylene, with a high molecular weight, usually between 2 and 6 million.

Roughened Surface Topography

The top surface 10, 110, 110a, 210, and 310 or bottom surface 20, 120, 120a, 220, and 320 of the implant 1, 101, 101a, 201, and 301 (or the top surface 81 of the integration plate 82 when present) may each have a roughened surface topography 80, 180, 180a, 280, 380, without sharp teeth that risk damage to bone structures, adapted to grip bone through friction generated when the implant 1, 101, 101a, 201, and 301 is placed between two vertebrae, inhibit migration of the implant 1, 101, 101a, 201, and 301, and optionally promote biological and chemical fusion (e.g., a biostimulating effect).

The ability to achieve spinal fusion is directly related to the available vascular contact area over which fusion is desired, the quality and quantity of the fusion mass, and the stability of the interbody spinal implant 1, 101, 101a, 201, and 301. The implants 1, 101, 101a, 201, and 301 allow for improved seating over the apophyseal rim of the vertebral body and better utilize this vital surface area over which fusion may occur and may better bear the considerable biomechanical loads presented through the spinal column with minimal interference with other anatomical or neurological spinal structures. The implants 1, 101, 101a, 201, and 301 may allow for improved visualization of implant seating and fusion assessment. The roughened surface topography 80, 180, 180a, 280, 380 helps to facilitate osteointegration (e.g., formation of a direct structural and functional interface between the artificial implant and living bone or soft tissue) with the surrounding living bone.

It is generally believed that the surface of an implant 1, 101, 101a, 201, and 301 determines its ultimate ability to integrate into the surrounding living bone. Without being limited by theory, it is hypothesized that the cumulative effects of at least implant composition, implant surface energy, and implant surface roughness play a major role in the biological response to, and osteointegration of, an implant device. Thus, implant fixation may depend, at least in part, on the stimulation and proliferation of bone modeling and forming cells, such as osteoclasts and osteoblasts and like-functioning cells upon the implant surface. Still further, it appears that these cells attach more readily to relatively rough surfaces rather than smooth surfaces. In this manner, a surface may be bioactive due to its ability to stimulate cellular attachment and osteointegration. The roughened surface topography 80, 180, 180a, 280, 380 described in this document may better promote the osteointegration of certain embodiments of the present invention. The roughened surface topography 80, 180, 180a, 280, 380 may also better grip the surfaces of the vertebral endplate 25 and inhibit implant migration upon placement and seating.

The implant 1, 101, 101a, 201, and 301 may include a roughened surface topography 80, 180, 180a, 280, 380 on at least a portion of one or more integration surfaces. As used in this document, the integration surface is the surface at least partially in contact with the vertebral or bone structure (e.g., the top surface 10, 110, 110a, 210, and 310 or bottom surface 20, 120, 120a, 220, and 320 of the implant 1, 101, 101a, 201, and 301 or the top surface 81, 381 of the integration plate 82, 382 when present).

The roughened surface topography 80, 180, 180a, 280, 380 preferably contains predefined surface features that (a) engage the vertebral endplates with a friction fit and, following an endplate preserving surgical technique, (b) attain initial stabilization, and (c) benefit fusion. The composition of the vertebral endplate 25 is a thin layer of notch-sensitive bone that is easily damaged by features (such as teeth) that protrude sharply from the surface of traditional implants. Avoiding such teeth and the attendant risk of damage, the roughened surface topography 80, 180, 180a, 280, 380 does not have teeth or other sharp, potentially damaging structures; rather, the roughened surface topography 80, 180, 180a, 280, 380 may have a pattern of repeating features of predetermined sizes, smooth shapes, and orientations. By "predetermined" is meant determined beforehand, so that the predetermined characteristic of the surface must be determined, i.e., chosen or at least known, before use of the implant 1, 101, 101a, 201, and 301.

The roughened surface topography 80, 180, 180a, 280, 380 may be comprised of macro features, micro features, and nano features. For example, the roughened surface topography 80, 180, 180a, 280, 380 may be obtained by combining separate macro processing, micro processing, and nano processing steps. The term "macro" typically means relatively large; for example, in the present application, dimensions measured in millimeters (mm). The term "micro" typically means one millionth ($10^{-6}$); for example, in the present application, dimensions measured in microns (μm) which correspond to $10^{-6}$ meters. The term "nano" typically means one billionth ($10^{-9}$); for example, in the present application, dimensions measured in nanometers (nm) which correspond to $10^{-9}$ meters.

The shapes of the frictional surface protrusions of the roughened surface topography 80, 180, 180a, 280, 380 may be formed using processes and methods commonly applied to remove metal during fabrication of implantable devices such as chemical, electrical, electrochemical, plasma, or laser etching; cutting and removal processes; casting; forging; machining; drilling; grinding; shot peening; abrasive media blasting (such as sand or grit blasting); and combinations of these subtractive processes. Additive processes such as welding, thermal, coatings, sputtering, and optical melt additive processes are also suitable. The resulting surfaces either can be random in the shape and location of the features or can have repeating patterns. This flexibility allows for the design and production of surfaces that resist motion induced by loading in specific directions that are beneficial to the installation process and resist the opposing forces that can be the result of biologic or patient activities such as standing, bending, or turning or as a result of other activities. The shapes of the surface features when overlapping increase the surface contact area but do not result in undercuts that generate a cutting or aggressively abrasive action on the contacting bone surfaces.

These designed surfaces are composed of various sizes of features that, at the microscopic level, interact with the tissues and stimulate their natural remodeling and growth. At a larger scale these features perform the function of generating non-stressful friction that, when combined with a surgical technique that retains the most rigid cortical bone structures in the disc space, allow for a friction fit that does not abrade, chip, perforate, or compromise the critical endplate structures. The features may be divided into three size scales: nano, micro, and macro. The overlapping of the three feature sizes can be achieved using manufacturing processes that are completed sequentially and, therefore, do not remove or degrade the previous method.

The first step in the process may be mechanical (e.g., machining though conventional processes) or chemical bulk removal, for example, to generate macro features. The macro features may be of any suitable shape, for example, roughly spherical in shape, without undercuts or protruding sharp edges. Other shapes are possible, such as ovals, polygons (including rectangles), and the like. These features may be at least partially overlapped with the next scale (micro) of features using either chemical or mechanical methods (e.g., $AlO_2$ blasting) in predetermined patterns which also do not result in undercuts or protruding sharp edges. The third and final process step is completed through more mild (less aggressive) etching (e.g., HCl acid etching) that, when completed, generates surface features in both the micro and nano scales over both of the features generated by the two previous steps. The nano layer dictates the final chemistry of the implant material.

Figure 20:
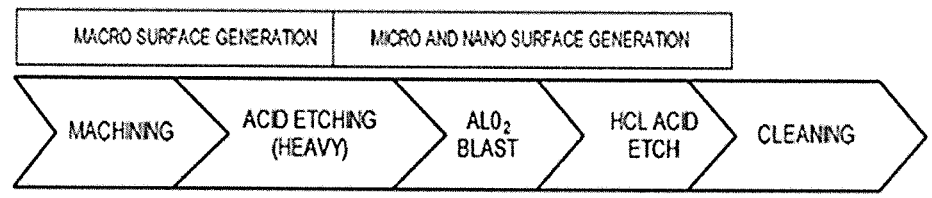
FIG. 20 illustrates examples of types of process steps that can be used to form macro, micro, or nano processes.

FIG. 20 illustrates one set of process steps that can be used to form the roughened surface topography 80, 180, 180a, 280, 380 according to an embodiment of the present invention. First, the part is machined, for example, from a bar stock comprising titanium, and a rough clean may be provided to remove any contaminants from machining. Second, the part may undergo a heavy acid etching (e.g., masked etching). Next, the part may undergo an abrasive blast, for example, using an alumina abrasive. The part may also undergo another acid etch, for example, with a solution comprising hydrochloric acid. Finally, the part may undergo a cleaning (e.g., with water and optionally a detergent). As illustrated, there may be some overlap in the processes that can be applied to form each of the three types of features (macro, micro, and nano). For example, acid etching can be used to form the macro features, then the same or a different acid etching process can be used to form the micro features.

(a) Macro Features

The macro features of the roughened surface topography 80, 180, 180a, 280, 380 are relatively large features (e.g., on the order of millimeters). The macro features may be formed from subtractive techniques (e.g., mechanical or chemical bulk removal, for example) or additive techniques (e.g., deposition). Preferably, the macro features are formed by subtractive techniques, which remove portions of the surface (e.g., from the base material that was used to form the implant 1, 101, 101a, 201, and 301). Suitable subtractive techniques may include, for example, machining (e.g., machine tools, such as saws, lathes, milling machines, and drill presses, are used with a sharp cutting tool to physically remove material to achieve a desired geometry) or masked etching (e.g., portions of the surface are protected by a "masking" material which resists etching and an etching substance is applied to unmasked portions). The patterns may be organized in regular repeating patterns and optionally overlap each other. In a preferred embodiment, the macro features may be formed in three, sequential steps.

The macro features may be produced by a heavy masked etching process, for example. Before etching, the surface may be cleaned and optionally blasted with an abrasive (e.g., alumina) in the areas to be chemically textured. Certain areas may be masked in a pattern using an etch resist and cured. The surface may then be chemically milled, for example, using a composition comprising hydrofluoric acid. The maskant and chemical milling may be repeated any number of times necessary to produce the desired pattern and etching depth. After the final etching process, the maskant may be removed and the part may be cleaned. The surface may also be passivated, for example, using an aqueous solution comprising nitric acid. The part may be cleaned and rinsed with water.

The macro features may be formed, for example, using three cut patterns. Specifically, a first cut pattern of the macro features may be formed in a surface (e.g., the top surface 10, 110, 110a, 210, and 310). The "cut 1" features of the first cut pattern may cover about 20% of the total area of the surface, for example, leaving about 80% of the original surface remaining. The range of these percentages may be about ±20%, preferably +10%, and more preferably about ±5%. The "cut 1" features of the first cut pattern do not have any undercuts. In one embodiment, these "cut 1" features have the smallest diameter and greatest depth of the macro features that are formed during the sequential steps.

A second cut pattern of the macro features may be formed in the surface. Together, the "cut 1" features of the first cut pattern and the "cut 2" features of the second cut pattern may cover about 85% of the total area of the surface, for example, leaving about 15% of the original surface remaining. The range of these percentages may be about ±10% and preferably ±5%. In an embodiment of the invention, these "cut 2" features have both a diameter and a depth between those of the "cut 1" and "cut 3" features of the macro features that are formed during the first and third steps of the process of forming the macro features of the roughened surface topography 80, 180, 180a, 280, 380.

A third cut pattern of the macro features may be formed in the surface. Together, the "cut 1" features of the first cut pattern, the "cut 2" features of the second cut pattern, and the "cut 3" features of the third cut pattern may cover about 95% of the total area of the surface, for example, leaving about 5% of the original surface remaining. The range of these percentages may be about ±1%. In an embodiment of the invention, these "cut 3" features may have the largest diameter and least depth of the macro features that are formed during the sequential process steps.

(b) Micro Features

After the macro features are formed, additional process steps may be sequentially applied, in turn, to form the micro surface features (e.g., on the order of micrometers) of the roughened surface topography 80, 180, 180a, 280, and 380. The micro features may also be formed from subtractive techniques (e.g., mechanical or chemical bulk removal, for example) or additive techniques (e.g., deposition). Preferably, the micro features are also formed by subtractive techniques.

In an exemplary embodiment, the micro features are removed by masked or unmasked etching, such as acid etching. For example, portions of the surface, including portions of the surface exposed by the macro step(s) described above, may be exposed to abrasive blasting, chemical etching, or both. In an exemplary embodiment, the micro process includes an acid etching, with a strong acid, such as hydrochloric acid (HCl), hydroiodic acid (HI), hydrobromic acid (HBr), hydrofluoric (HF), perchloric acid ($HClO_4$), nitric acid ($HNO_3$), sulfuric acid ($H_2SO_4$), and the like. Preferably, the acid etching uses an aqueous solution comprising hydrochloric acid. The etching process may be repeated a number of times as necessitated by the amount and nature of the irregularities required for any particular application. Control of the strength of the etchant material, the temperature at which the etching process takes place, and the time allotted for the etching process allows fine control over the resulting surface produced by the process. The number of repetitions of the etching process can also be used to control the surface features. For example, the roughened surface topography 80, 180, 180a, 280, and 380 may be obtained via the repetitive masking and chemical or electrochemical milling processes described in U.S. Pat. Nos. 5,258,098; 5,507,815; 5,922,029; and 6,193,762, the contents of which are incorporated by reference into this document, in their entirety, and for all purposes.

By way of example, an etchant mixture of at least one of nitric acid and hydrofluoric acid may be repeatedly applied to a titanium surface to produce an average etch depth of about 0.53 mm. In another example, chemical modification of titanium can be achieved using at least one of hydrofluoric acid, hydrochloric acid, and sulfuric acid. In a dual acid etching process, for example, the first exposure is to hydrofluoric acid and the second is to a hydrochloric acid and sulfuric acid mixture. Chemical acid etching alone may enhance osteointegration without adding particulate matter (e.g., hydroxyapatite) or embedding surface contaminants (e.g., grit particles).

In one embodiment, the micro features are created by abrasive or grit blasting, for example, by applying a stream of abrasive material (such as alumina, sand, and the like) to the surface. In an exemplary embodiment, the micro features are created, at least partially, with an aqueous hydrochloric acid etching step and at least partially with an $AlO_2$ blasting step. Patterns may be organized in regular repeating patterns and optionally overlap each other. After the micro features are formed, it is possible that less than about 3% of the original surface remains. The range of that percentage may be about ±1%.

(c) Nano Features

After the macro features and micro features are formed, additional process steps may be sequentially applied, in turn, to form the nano surface features (e.g., on the order of nanometers) of the roughened surface topography 80, 180, 180a, 280, and 380. The nano features may also be formed from subtractive techniques (e.g., mechanical or chemical bulk removal, for example) or additive techniques (e.g., deposition). Preferably, the nano features are also formed by subtractive techniques.

In an exemplary embodiment, the nano features are removed by masked or unmasked etching. For example, portions of the surface, including portions of the surface exposed by the macro and micro steps described above, may be exposed to a chemical etching. In an exemplary embodiment, the nano process also includes an acid etching, with a strong or weak acid, such as hydrochloric acid (HCl), hydroiodic acid (HI), hydrobromic acid (HBr), hydrofluoric (HF), perchloric acid ($HClO_4$), nitric acid ($HNO_3$), sulfuric acid ($H_2SO_4$), and the like. The acid etching process for the nano step is preferably less aggressive than the acid etching process in the macro or micro steps. In other words, a less acidic, mild, or more diluted acid may be selected. In an exemplary embodiment, the nano features are created, at least partially, with an aqueous hydrochloric acid etching step.

As an example, the nano features (or micro features) may be formed by preparing an acid solution comprising hydrochloric acid, water, and titanium; applying the acid solution to the surface; removing the acid solution by rinsing with water; and heating and subsequently cooling the surface.

The acid solution may be prepared using any suitable techniques known in the art. For example, the acid solution may be prepared by combining hydrochloric acid and water, simultaneously or sequentially. The aqueous hydrochloric acid solution may optionally be heated, for example, to a temperature of about 150-250° F. (66-121° C.), preferably about 200-210° F. (93-99° C.), and most preferably about 205° F. (96° C.). The titanium may be seeded (e.g., added) in the aqueous hydrochloric acid solution or may already be present from titanium previously removed from at least one surface of the implant, for example, in a continuous manufacturing process. The solution may optionally be cooled. The acid solution may comprise a concentration of 20-40% hydrochloric acid, preferably about 25-31% hydrochloric acid, and more preferably about 28% hydrochloric acid, based on the weight percent of the solution.

The acid solution may be applied to the surface using any suitable mechanism or techniques known in the art, for example, immersion, spraying, brushing, and the like. In an exemplary embodiment, the acid solution is applied by immersing the entire part in the solution. It is also contemplated that the surface may be immersed in the acid solution alone or in combination with the assembled implant 1, 101, 101a, 201, and 301. If desired, certain areas of the surface or the implant 1, 101, 101a, 201, and 301 may be masked in patterns or to protect certain portions of the implant 1, 101, 101a, 201, and 301. The acid solution may be heated when it is applied. For example, the solution may be heated to a temperature of about 150-250° F. (66-121° C.), preferably about 200-210° F. (93-99° C.), and most preferably about 205° F. (96° C.). The solution may also be applied for any suitable period of time. For example, the solution may be applied for a period of time of about 5-30 minutes, preferably about 15-25 minutes, and more preferably about 20 minutes.

After the acid solution is applied, the acid solution may be removed, for example, by rinsing with water (e.g., deionized water). The surface or entire implant 1, 101, 101a, 201, and 301 may be subsequently dried. The surface may be dried using any suitable mechanism or techniques known in the art, for example, by heating in an oven (e.g., a dry oven). The surface may be heated to a temperature of about 110-130° F. (43-54° C.), preferably about 120-125° F. (49-52° C.), and most preferably about 122.5° F. (50° C.). The surface may be heated for any suitable period of time, for example about 30-50 minutes, preferably about 35-45 minutes, and more preferably about 40 minutes. After heating, the surface may be cooled to room temperature, for example.

It is contemplated that the nano features may also be created by the abrasive or grit blasting, for example, described for the micro processing step. Patterns may be organized in regular repeating patterns and optionally overlap each other. The nano features may also be achieved by tumble finishing (e.g., tumbling) the part or the implant 1, 101, 101a, 201, and 301. Suitable equipment and techniques can be selected by one of ordinary skill in the art. For example, a barrel may be filled with the parts or implants 1, 101, 101a, 201, and 301 and the barrel is then rotated. The parts or implants 1, 101, 101a, 201, and 301 may be tumbled against themselves or with steel balls, shot, rounded-end pins, ballcones, or the like. The tumbling process may be wet (e.g., with a lubricant) or dry. After the nano features are formed, it is possible that less than about 1% of the original surface remains. For example, after the nano features are formed, the roughened surface topography 80, 180, 180a, 280, and 380 may cover substantially all of the top surface 10, 110, 110a, 210, and 310 and/or bottom surface 20, 120, 120a, 220, and 320 of the implant 1, 101, 101a, 201, and 301.

Any or each of the steps, including the macro, micro, or nano processing steps, may be accompanied by a cleaning step. In addition, the part may be cleaned once the processing steps are complete. For example, the part may be washed in an aqueous environment under agitation and heat with or without a detergent. Following washing, the part may be dried, for example with hot air, heating in a dry oven, or both.

As should be readily apparent to a skilled artisan, the process steps described in this document can be adjusted to create a mixture of depths, diameters, feature sizes, and other geometries suitable for a particular implant application. The orientation of the pattern of features can also be adjusted. Such flexibility is desirable, especially because the ultimate pattern of the roughened surface topography 80, 180, 180a, 280, and 380 of the implant 1, 101, 101a, 201, and 301 should be oriented in opposition to the biologic forces on the implant 1, 101, 101a, 201, and 301 and to the insertion direction. In one particular embodiment, for example, the pattern of the roughened surface topography 80, 180, 180a, 280, and 380 may be modeled after an S-shaped tire tread.

Roughness Parameters

Several separate parameters can be used to characterize the roughness of an implant surface. Among those parameters are the average amplitude, Ra; the maximum peak-to-valley height, Rmax; and the mean spacing, Sm. Each of these three parameters, and others, are explained in detail below. Surface roughness may be measured using a laser profilometer or other standard instrumentation.

In addition to the parameters Ra, Rmax, and Sm mentioned above, at least two other parameters can be used to characterize the roughness of an implant surface. In summary, the five parameters are: (1) average amplitude, Ra; (2) average peak-to-valley roughness, Rz; (3) maximum peak-to-valley height, Rmax; (4) total peak-to-valley of waviness profile, Wt; and (5) mean spacing, Sm. Each parameter is explained in detail as follows.

1. Average Amplitude Ra

Figure 21:
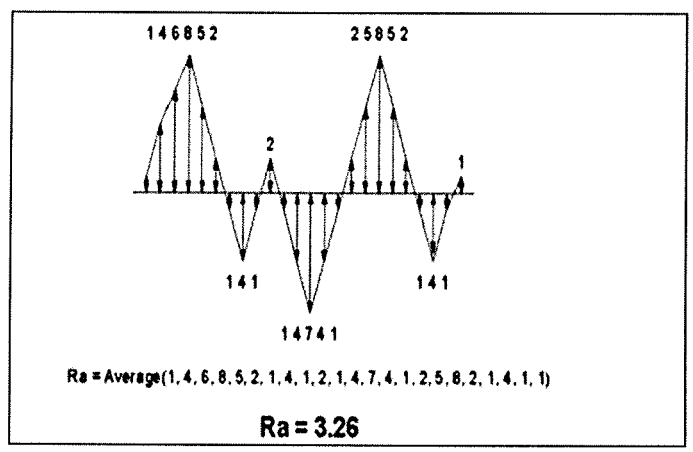
FIG. 21 graphically represents the average amplitude, Ra.

In practice, "Ra" is the most commonly used roughness parameter. It is the arithmetic average height. Mathematically, Ra is computed as the average distance between each roughness profile point and the mean line. In FIG. 21, the average amplitude is the average length of the arrows.

In mathematical terms, this process can be represented as $$Ra = \frac{1}{n}\sum_{i=1}^{n}|y_i|$$

2. Average Peak-to-Valley Roughness Rz

Figure 22:
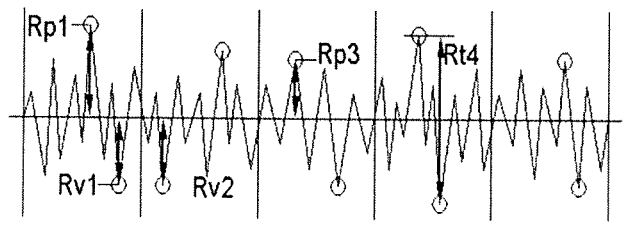
FIG. 22 graphically represents the average peak-to-valley roughness, Rz.

The average peak-to-valley roughness, Rz, is defined by the ISO and ASME 1995 and later. Rz is based on one peak and one valley per sampling length. The RzDIN value is based on the determination of the peak-to-valley distance in each sampling length. These individual peak-to-valley distances are averaged, resulting in the RzDIN value, as illustrated in FIG. 22.

3. Maximum Peak-to-Valley Height Rmax

Figure 23:
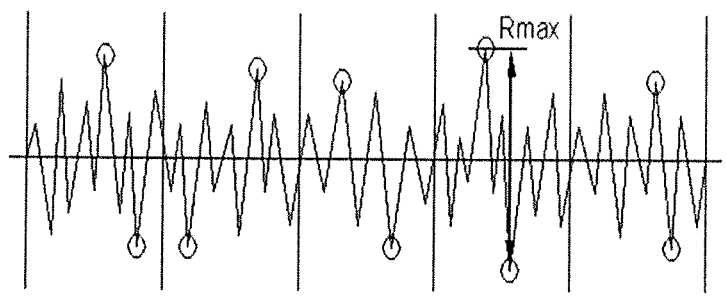
FIG. 23 graphically represents the maximum peak-to-valley height, Rmax.

The maximum peak-to-valley height, Rmax, is the maximum peak-to-valley distance in a single sampling length—as illustrated in FIG. 23.

4. Total Peak-to-Valley of Waviness Profile Wt

Figure 24:
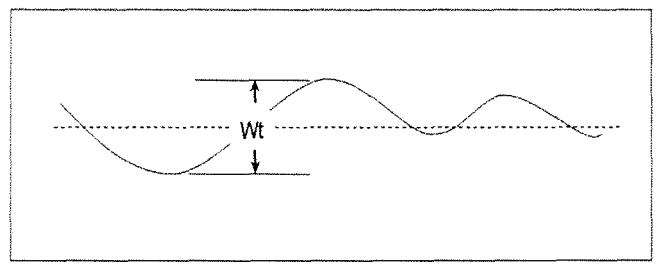
FIG. 24 graphically represents the total peak-to-valley of waviness profile.

The total peak-to-valley of waviness profile (over the entire assessment length) is illustrated in FIG. 24.

5. Mean Spacing Sm

Figure 25:
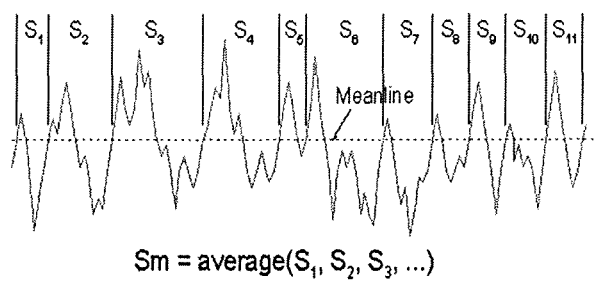
FIG. 25 graphically represents the mean spacing, Sm.

The mean spacing, Sm, is the average spacing between positive mean line crossings. The distance between each positive (upward) mean line crossing is determined and the average value is calculated, as illustrated in FIG. 25.

The parameters Sm, Rmax, and Ra can be used define the surface roughness following formation of each of the three types of features macro, micro, and nano. Such data are provided in Table 1 below.

TABLE 1

EXAMPLE DATA BY PROCESS STEP

| | Size (Sm) | Depth (Rmax) | Roughness (Ra) |
|---|---|---|---|
| Surface Feature Size and Roughness (Metric): Macro (μm) | | | |
| Max. | 2,000 | 500 | 200 |
| Min. | 400 | 40 | 20 |
| Avg. | 1,200 | 270 | 110 |
| Surface Feature Size and Roughness (Metric): Micro (μm) | | | |
| Max. | 400 | 40 | 20 |
| Min. | 20 | 2 | 1 |
| Avg. | 210 | 11 | 5.5 |
| Surface Feature Size and Roughness (Metric): Nano (μm) | | | |
| Max. | 20 | 2 | 1 |
| Min. | 0.5 | 0.2 | 0.01 |
| Avg. | 10.25 | 1.1 | 0.505 |

From the data in Table 1, the following preferred ranges (all measurements in microns) can be derived for the macro features for each of the three parameters. The mean spacing, Sm, is between about 400-2,000, with a range of 750-1,750 preferred and a range of 1,000-1,500 most preferred. The maximum peak-to-valley height, Rmax, is between about 40-500, with a range of 150-400 preferred and a range of 250-300 most preferred. The average amplitude, Ra, is between about 20-200, with a range of 50-150 preferred and a range of 100-125 most preferred.

The following preferred ranges (all measurements in microns) can be derived for the micro features for each of the three parameters. The mean spacing, Sm, is between about 20-400, with a range of 100-300 preferred and a range of 200-250 most preferred. The maximum peak-to-valley height, Rmax, is between about 2-40, with a range of 2-20 preferred and a range of 9-13 most preferred. The average amplitude, Ra, is between about 1-20, with a range of 2-15 preferred and a range of 4-10 most preferred.

The following preferred ranges (all measurements in microns) can be derived for the nano features for each of the three parameters. The mean spacing, Sm, is between about 0.5-20, with a range of 1-15 preferred and a range of 5-12 most preferred. The maximum peak-to-valley height, Rmax, is between about 0.2-2, with a range of 0.2-1.8 preferred and a range of 0.3-1.3 most preferred. The average amplitude, Ra, is between about 0.01-1, with a range of 0.02-0.8 preferred and a range of 0.03-0.6 most preferred.

Example Surgical Methods

The following examples of surgical methods are included to more clearly demonstrate the overall nature of the invention. These examples are exemplary, not restrictive, of the invention.

Certain embodiments of the invention are particularly suited for use during interbody spinal implant procedures currently known in the art. For example, the disc space may be accessed using a standard mini open retroperitoneal laparotomy approach. The center of the disc space is located by AP fluoroscopy taking care to make sure the pedicles are equidistant from the spinous process. The disc space is then incised by making a window in the annulus for insertion of certain embodiments of the spinal implant 1, 101, 101a, 201, and 301 (a 32 or 36 mm window in the annulus is typically suitable for insertion). The process according to the invention minimizes, if it does not eliminate, the cutting of bone. The endplates are cleaned of all cartilage with a curette, however, and a size-specific rasp (or broach) may then be used.

Use of a rasp preferably substantially minimizes or eliminates removal of bone, thus substantially minimizing or eliminating impact to the natural anatomical arch, or concavity, of the vertebral endplate while preserving much of the apophyseal rim. Preservation of the anatomical concavity is particularly advantageous in maintaining biomechanical integrity of the spine. For example, in a healthy spine, the transfer of compressive loads from the vertebrae to the spinal disc is achieved via hoop stresses acting upon the natural arch of the endplate. The distribution of forces, and resultant hoop stress, along the natural arch allows the relatively thin shell of subchondral bone to transfer large amounts of load.

During traditional fusion procedures, the vertebral endplate natural arch may be significantly removed due to excessive surface preparation for implant placement and seating. This is especially common where the implant is to be seated near the center of the vertebral endplate or the implant is of relatively small medial-lateral width. Breaching the vertebral endplate natural arch disrupts the biomechanical integrity of the vertebral endplate such that shear stress, rather than hoop stress, acts upon the endplate surface. This redistribution of stresses may result in subsidence of the implant 1, 101, 101a, 201, and 301 into the vertebral body.

Preferred embodiments of the surgical method minimize endplate bone removal on the whole, while still allowing for some removal along the vertebral endplate far lateral edges where the subchondral bone is thickest. Still further, certain embodiments of the interbody spinal implant 1, 101, 101a, 201, and 301 include smooth, rounded, and highly radiused posterior portions and lateral sides which may minimize extraneous bone removal for endplate preparation and reduce localized stress concentrations. Thus, the interbody surgical implant 1, 101, 101a, 201, and 301 and methods of using it are particularly useful in preserving the natural arch of the vertebral endplate and minimizing the chance of implant subsidence.

Because the endplates are spared during the process of inserting the spinal implant 1, 101, 101a, 201, and 301, hoop stress of the inferior and superior endplates is maintained. Spared endplates allow the transfer of axial stress to the apophasis. Endplate flexion allows the bone graft placed in the interior of the spinal implant 1, 101, 101a, 201, and 301 to accept and share stress transmitted from the endplates. In addition, spared endplates minimize the concern that BMP might erode the cancellous bone.

The interbody spinal implant 1, 101, 101a, 201, and 301 is durable and can be impacted between the endplates with standard instrumentation. Therefore, certain embodiments of the invention may be used as the final distractor during implantation. In this manner, the disc space may be under-distracted (e.g., distracted to some height less than the height of the interbody spinal implant 1) to facilitate press-fit implantation. Further, certain embodiments of the current invention having a smooth and rounded posterior portion (and lateral sides) may facilitate easier insertion into the disc space. Still further, the surface roughened topography 80, 180, 180a, 280, 380 may lessen the risk of excessive bone removal during distraction as compared to implants having teeth, ridges, or threads currently known in the art even in view of a press-fit surgical distraction method. Nonetheless, once implanted, the interbody surgical implant 1, 101, 101a, 201, and 301 may provide secure seating and prove difficult to remove. Thus, certain embodiments of the interbody spinal implant 1, 101, 101a, 201, and 301 may maintain a position between the vertebral endplates 25 due, at least in part, to resultant annular tension attributable to press-fit surgical implantation and, post-operatively, improved osteointegration at one or both of the outer surfaces (e.g., top 10 or bottom 20 surfaces).

Surgical implants and methods tension the vertebral annulus via distraction. These embodiments and methods may also restore spinal lordosis, thus improving sagittal and coronal alignment. Implant systems currently known in the art require additional instrumentation, such as distraction plugs, to tension the annulus. These distraction plugs require further tertiary instrumentation, however, to maintain the lordotic correction during actual spinal implant insertion. If tertiary instrumentation is not used, then some amount of lordotic correction may be lost upon distraction plug removal. The interbody spinal implant 1, 101, 101a, 201, and 301, according to certain embodiments of the invention, is particularly advantageous in improving spinal lordosis without the need for tertiary instrumentation, thus reducing the instrument load upon the surgeon. This reduced instrument load may further decrease the complexity, and required steps, of the implantation procedure.

Certain embodiments of the spinal implant 1, 101, 101a, 201, and 301 may also reduce deformities (such as isthmic spondylolythesis) caused by distraction implant methods. Traditional implant systems require secondary or additional instrumentation to maintain the relative position of the vertebrae or distract collapsed disc spaces. In contrast, interbody spinal implant 1, 101, 101a, 201, and 301 may be used as the final distractor and thus maintain the relative position of the vertebrae without the need for secondary instrumentation.

Certain embodiments collectively comprise a family of implants, each having a common design philosophy. These implants and the associated surgical techniques have been designed to address at least the ten, separate challenges associated with the current generation of traditional anterior spinal fusion devices listed above in the Background section of this document.

After desired annulotomy and discectomy, embodiments of the invention first adequately distract the disc space by inserting (through impaction) and removing sequentially larger sizes of very smooth distractors, which have been size matched with the size of the available implant 1, 101, 101*a*, 201, and 301. Once adequate distraction is achieved, the surgeon prepares the end-plate with a rasp. There is no secondary instrumentation required to keep the disc space distracted while the implant 1, 101, 101*a*, 201, and 301 is inserted, as the implant 1, 101, 101*a*, 201, and 301 has sufficient mechanical strength that it is impacted into the disc space. In fact, the height of the implant 1, 101, 101*a*, 201, and 301 is preferably about 1 mm greater than the height of the rasp used for end-plate preparation, to create some additional tension in the annulus by implantation, which creates a stable implant construct in the disc space.

The implant geometry has features which allow it to be implanted via any one of an anterior, antero-lateral, or lateral approach, providing tremendous intra-operative flexibility of options. The implant 1, 101, 101*a*, 201, and 301 has adequate strength to allow impact, and the sides of the implant 1, 101, 101*a*, 201, and 301 may have smooth surfaces to allow for easy implantation and, specifically, to prevent binding of the implant 1, 101, 101*a*, 201, and 301 to soft tissues during implantation.

The invention encompasses a number of different implant 1, 101, 101*a*, 201, and 301 configurations, including a composite implant formed of top and optional bottom plates (components), for example, made out of titanium. The integration surfaces exposed to the vertebral body have a roughened surface topography 80, 180, 180*a*, 280, 380 to allow for bony in-growth over time, and to provide resistance against expulsion. The top and bottom titanium plates may be assembled together with the implant body. The net result is a composite implant that has engineered stiffness for its clinical application. The axial load may be borne by the polymeric component of the construct.

It is believed that an intact vertebral end-plate deflects like a diaphragm under axial compressive loads generated due to physiologic activities. If a spinal fusion implant is inserted in the prepared disc space via a procedure which does not destroy the end-plates, and if the implant contacts the end-plates only peripherally, the central dome of the end-plates can still deflect under physiologic loads. This deflection of the dome can pressurize the bone graft material packed inside the spinal implant, hence allowing it to heal naturally. The implant 1, 101, 101*a*, 201, and 301 designed according to certain embodiments allows the vertebral end-plate to deflect and allows healing of the bone graft into fusion.

Although illustrated and described above with reference to certain specific embodiments and examples, the present invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges. In addition, features of one embodiment may be incorporated into another embodiment.

What is claimed is:

1. An interbody spinal implant, comprising a top surface, a bottom surface, with at least one of the top surface and the bottom surface including a roughened surface topography, at least one self-deploying anchor positioned substantially centrally on the top surface, and at least one self-deploying anchor positioned substantially centrally on the bottom surface, with each self-deploying anchor comprising a locking bar comprising a locking tip, the locking bar being connected to a connecting piece via a first arcuate member and the connecting piece being connected to an expulsion tab via a second arcuate member, the expulsion tab having a bone-engaging tip and an interior surface comprising one or more protrusions that engage the locking tip and thereby prevent the anchor from retracting once the anchor has deployed.

2. The interbody spinal implant of claim 1, wherein each self-deploying anchor comprises a temperature-sensitive metal alloy having a transformation temperature.

3. The interbody spinal implant of claim 2, wherein the expulsion tab is deployed when the implant is raised to or above the transformation temperature.

4. The interbody spinal implant of claim 2, wherein the temperature-sensitive metal alloy comprises nitinol.

5. The interbody spinal implant of claim 1, wherein each self-deploying anchor comprises a shape memory material.

6. The interbody spinal implant of claim 1, wherein the expulsion tab comprises an exterior surface comprising a roughened surface topography, and the exterior surface of the expulsion tab is substantially coplanar with the top surface or the bottom surface of the implant when the anchor is not deployed.

7. The interbody spinal implant of claim 1, wherein the connecting piece and second arcuate member define a connection bore through the anchor.

8. The interbody spinal implant of claim 1, wherein the interior surface of the expulsion tab comprises a ratchet system having a plurality of protrusions each separated by a recess.

9. The interbody spinal implant of claim 7, wherein each self-deploying anchor is affixed to the implant with a pin, bolt, or shaft, which extends through the connection bore.

10. The interbody spinal implant of claim 9, wherein each self-deploying anchor is affixed to the implant further with a second pin, bolt, or shaft, which extends through an opening defined by the locking bar being connected to the connecting piece via the first arcuate member.

11. The interbody spinal implant of claim 1, wherein the implant comprises at least three self-deploying anchors.

12. The interbody spinal implant of claim 11, wherein the implant comprises at least three self-deploying anchors on the top surface, and at least three self-deploying anchors on the bottom surface.

13. The interbody spinal implant of claim 1, wherein the top surface and the bottom surface each comprises a first self-deploying anchor and a second self-deploying anchor, with the first self-deploying anchor oriented in an opposite direction relative to the second self-deploying anchor.

14. The interbody spinal implant of claim 13, wherein the bone-engaging tip of the first self-deploying anchor on the to surface and on the bottom surface is oriented substantially toward the anterior portion of the implant and the bone-engaging tip of the second self-deploying anchor on the top surface and on the bottom surface is oriented substantially toward the posterior portion of the implant.

15. The interbody spinal implant of claim 1, wherein the implant comprises a substantially hollow center and a single vertical aperture.

16. The interbody spinal implant of claim 15, wherein the single vertical aperture (a) extends from the top surface to the bottom surface, (b) has a size and shape predetermined to maximize the surface area of the top surface and the bottom surface available proximate the anterior and posterior portions while maximizing both radiographic visualization and access to the substantially hollow center, and (c) defines a transverse rim.

17. The interbody spinal implant of claim 1, wherein the roughened surface topography comprises micro features and nano features.

18. The interbody spinal implant of claim 17, wherein the micro features comprise a peak-to-valley height between about 2-40 microns, and the nano features comprise a peak-to-valley height between about 0.2-2 microns.

19. The interbody spinal implant of claim 1, wherein the implant comprises titanium.

20. The interbody spinal implant of claim 1, wherein the implant comprises a first integration plate and optionally a second integration plate affixed to the top surface, the bottom surface, or both surfaces of the implant.

21. The interbody spinal implant of claim 1, further comprising opposing lateral sides and opposing anterior and posterior portions, wherein the roughened surface topography is without sharp teeth that risk damage to bone structures, and is adapted to grip bone through friction generated when the implant is placed between two vertebrae and to inhibit migration of the implant.

22. The interbody spinal implant of claim 6, wherein the roughened surface topography of the exterior surface of the expulsion tab comprises micro features and nano features.

23. The interbody spinal implant of claim 22, wherein the roughened surface topography of the exterior surface of the expulsion tab comprises micro features comprising a peak-to-valley height between about 2-40 microns, and nano features comprising a peak-to-valley height between about 0.2-2 microns.

\* \* \* \* \*